(12) United States Patent
Lee et al.

(10) Patent No.: US 11,491,265 B2
(45) Date of Patent: Nov. 8, 2022

(54) MECHANICAL VACUUM DRESSING FOR MECHANICALLY MANAGING, PROTECTING AND SUCTIONING SMALL INCISIONAL WOUNDS

(71) Applicant: Cornell University, Ithaca, NY (US)

(72) Inventors: Sang Lee, New York, NY (US); Anthony Assal, Corona, NY (US); Matthew Baird, Tarrytown, NY (US); John Frederick Cornhill, New York, NY (US); Russell Corwin, Ossining, NY (US); Andrew Harvey, New York, NY (US); Jeffrey Milsom, New York, NY (US); Anh Nguyen, Woburn, MA (US); Jia Xing, Long Island City, NY (US); James Goldie, Pepperell, MA (US); Vladimir Gilman, Pepperell, MA (US); Minh Duong, Pepperell, MA (US); Jennifer Vondran, Pepperell, MA (US); Blair Hough, Pepperell, MA (US); Gerard I. Libby, Peabody, MA (US); Timothy Norman Johnson, Freeport, ME (US); Darwin T. Keith-Lucas, Arlington, MA (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 16/486,763

(22) PCT Filed: Feb. 22, 2018

(86) PCT No.: PCT/US2018/019172
§ 371 (c)(1),
(2) Date: Aug. 16, 2019

(87) PCT Pub. No.: WO2018/156730
PCT Pub. Date: Aug. 30, 2018

(65) Prior Publication Data
US 2019/0365962 A1 Dec. 5, 2019

Related U.S. Application Data
(60) Provisional application No. 62/462,267, filed on Feb. 22, 2017.

(51) Int. Cl.
*A61M 1/00* (2006.01)
*A61F 13/00* (2006.01)

(52) U.S. Cl.
CPC ..... *A61M 1/0011* (2013.01); *A61F 13/00068* (2013.01); *A61M 1/0003* (2013.01); *A61M 1/962* (2021.05); *A61M 2205/075* (2013.01)

(58) Field of Classification Search
CPC ...... A61M 1/00; A61M 1/962; A61M 1/0003; A61M 2005/5046; A61M 2005/3128;
(Continued)

(56) References Cited

U.S. PATENT DOCUMENTS 3,486,504 A  12/1969  Austin, Jr.
3,874,387 A   4/1975  Barbieri
(Continued)

FOREIGN PATENT DOCUMENTS

CN      105457110      4/2016
WO   WO 2007/068477    6/2007
(Continued)

OTHER PUBLICATIONS

Argenta et al., Vacuum-Assisted Closure: A New Method for Wound Control and Treatment: Clinical Experience, Annals of Plastic Surgery, Jun. 1997, vol. 38, No. 6, 563-577.
(Continued)

*Primary Examiner* — Tatyana Zalukaeva
*Assistant Examiner* — Nhu Q. Tran
(74) *Attorney, Agent, or Firm* — Pandiscio & Pandiscio

(57) ABSTRACT

A mechanical vacuum dressing comprising: a first valve layer comprising a first one-way valve; a second valve layer comprising a second one-way valve; the first valve layer being joined to the second valve layer so as to define a chamber therebetween; the first one-way valve being configured to admit fluid into the chamber through the first one-way valve but prevent fluid from exiting the chamber through the first one-way valve; the second one-way valve being configured to exhaust fluid from the chamber through the second one-way valve but prevent fluid from entering the chamber through the second one-way valve; and the second valve layer comprising an elastomeric material such that (i) when the second valve layer is moved away from the first valve layer, the volume of the chamber is increased, and (ii) when the second valve layer is thereafter released, the second valve layer moves back towards the first valve layer and the volume of the chamber is decreased.

27 Claims, 35 Drawing Sheets

(58) Field of Classification Search
CPC .. A61M 2039/0666; A61M 2039/2433; A61M 2039/064; A61M 2039/2426
See application file for complete search history.

(56) References Cited

U.S. PATENT DOCUMENTS

| | | | |
|---|---|---|---|
| 3,938,514 | A | 2/1976 | Boucher |
| 4,073,294 | A | 2/1978 | Stanley et al. |
| 4,465,062 | A | 8/1984 | Versaggi et al. |
| 4,997,438 | A | 3/1991 | Nipper |
| 5,263,922 | A | 11/1993 | Sova et al. |
| 5,454,779 | A | 10/1995 | Lurie et al. |
| 5,478,333 | A | 12/1995 | Asherman, Jr. |
| 5,549,584 | A * | 8/1996 | Gross ............... A61M 1/82 604/313 |
| 5,562,107 | A | 10/1996 | Lavender et al. |
| 5,589,256 | A | 12/1996 | Hansen et al. |
| 5,636,643 | A | 6/1997 | Argenta et al. |
| 5,645,081 | A | 7/1997 | Argenta et al. |
| 5,788,463 | A | 8/1998 | Chan |
| 6,431,212 | B1 * | 8/2002 | Hayenga ............ F16K 99/0046 137/855 |
| 6,936,037 | B2 | 8/2005 | Bubb et al. |
| 6,951,553 | B2 | 10/2005 | Bubb et al. |
| 7,070,584 | B2 | 7/2006 | Johnson et al. |
| 7,290,660 | B2 | 11/2007 | Tilman et al. |
| 7,338,482 | B2 | 3/2008 | Lockwood et al. |
| 7,534,039 | B2 | 5/2009 | Wu |
| 7,569,742 | B2 | 8/2009 | Haggstrom et al. |
| 7,699,823 | B2 | 4/2010 | Haggstrom et al. |
| 7,763,769 | B2 | 7/2010 | Johnson et al. |
| 7,790,945 | B1 | 9/2010 | Watson, Jr. |
| 7,794,438 | B2 | 9/2010 | Henley et al. |
| 7,838,717 | B2 | 11/2010 | Haggstrom et al. |
| 7,874,731 | B2 | 1/2011 | Turvey et al. |
| 7,909,805 | B2 | 3/2011 | Weston |
| 7,942,866 | B2 | 5/2011 | Radl et al. |
| 7,951,100 | B2 | 5/2011 | Hunt et al. |
| 7,964,766 | B2 | 6/2011 | Blott et al. |
| 8,084,664 | B2 | 12/2011 | Johnson et al. |
| 8,187,210 | B2 | 5/2012 | Hunt et al. |
| 8,188,331 | B2 | 5/2012 | Barta et al. |
| 8,202,002 | B2 | 6/2012 | McMahon et al. |
| 8,212,100 | B2 | 7/2012 | Moore |
| 8,257,326 | B2 | 9/2012 | Vitaris |
| 8,337,474 | B2 | 12/2012 | Hu et al. |
| 8,353,928 | B2 | 1/2013 | Joshi |
| 8,439,894 | B1 | 5/2013 | Miller |
| 8,460,255 | B2 | 6/2013 | Joshi et al. |
| 8,460,257 | B2 | 6/2013 | Locke et al. |
| 8,535,283 | B2 | 9/2013 | Heaton et al. |
| 8,545,466 | B2 | 10/2013 | Andresen et al. |
| 8,545,469 | B2 | 10/2013 | Andresen et al. |
| 8,569,566 | B2 | 10/2013 | Blott et al. |
| 8,604,265 | B2 | 12/2013 | Locke et al. |
| 8,632,523 | B2 | 1/2014 | Eriksson et al. |
| 8,679,079 | B2 | 3/2014 | Heaton et al. |
| 8,680,360 | B2 | 3/2014 | Greener et al. |
| 8,735,644 | B2 | 5/2014 | Johnson et al. |
| 8,764,732 | B2 | 7/2014 | Hartwell |
| 8,771,244 | B2 | 7/2014 | Eckstein et al. |
| 8,961,481 | B2 | 2/2015 | Hu et al. |
| 9,033,942 | B2 | 5/2015 | Vess |
| 9,265,665 | B2 | 2/2016 | Robinson et al. |
| 9,302,033 | B2 | 4/2016 | Riesinger |
| 9,427,502 | B2 | 8/2016 | Robinson et al. |
| 9,427,505 | B2 | 8/2016 | Askem et al. |
| 9,545,465 | B2 | 1/2017 | Allen et al. |
| 9,717,829 | B2 | 8/2017 | Eriksson et al. |
| 9,820,888 | B2 | 11/2017 | Greener et al. |
| 9,895,471 | B2 | 2/2018 | Hu et al. |
| 9,925,313 | B2 | 3/2018 | Weston |
| 9,968,488 | B2 | 5/2018 | Zamierowski et al. |
| 10,548,776 | B2 | 2/2020 | Greener et al. |
| 10,610,414 | B2 | 4/2020 | Hartwell et al. |
| 10,653,823 | B2 | 5/2020 | Bharti et al. |
| 2001/0029956 | A1 | 10/2001 | Argenta et al. |
| 2002/0111576 | A1 | 8/2002 | Greene et al. |
| 2003/0188754 | A1 | 10/2003 | Heaton et al. |
| 2004/0033750 | A1 | 2/2004 | Everett et al. |
| 2004/0054313 | A1 | 3/2004 | Molan |
| 2005/0070835 | A1 | 3/2005 | Joshi |
| 2005/0101940 | A1 * | 5/2005 | Radl ............... A61F 13/00068 604/543 |
| 2005/0143697 | A1 | 6/2005 | Riesinger |
| 2005/0175649 | A1 | 8/2005 | Disalvo et al. |
| 2006/0076069 | A1 | 4/2006 | Haamer |
| 2006/0079852 | A1 | 4/2006 | Bubb et al. |
| 2008/0003274 | A1 | 1/2008 | Kaiser |
| 2008/0306456 | A1 * | 12/2008 | Riesinger ............ A61M 1/08 604/316 |
| 2009/0299256 | A1 | 12/2009 | Barta et al. |
| 2009/0326430 | A1 | 12/2009 | Frederiksen et al. |
| 2010/0063483 | A1 | 3/2010 | Adahan |
| 2010/0137775 | A1 | 6/2010 | Hu et al. |
| 2010/0160901 | A1 | 6/2010 | Hu et al. |
| 2010/0191197 | A1 | 7/2010 | Braga et al. |
| 2010/0286635 | A1 | 11/2010 | Watson, Jr. |
| 2010/0305490 | A1 | 12/2010 | Coulthard et al. |
| 2010/0305524 | A1 | 12/2010 | Vess et al. |
| 2011/0087177 | A2 | 4/2011 | Weston |
| 2011/0106030 | A1 * | 5/2011 | Scholz ............... A61M 1/90 604/319 |
| 2011/0112492 | A1 * | 5/2011 | Bharti ............. A61F 13/0216 604/319 |
| 2011/0137270 | A1 | 6/2011 | Hu et al. |
| 2012/0035562 | A1 | 2/2012 | Locke et al. |
| 2012/0041401 | A1 | 2/2012 | Chao et al. |
| 2012/0316538 | A1 | 12/2012 | Heiser et al. |
| 2013/0046223 | A1 | 2/2013 | Schrammel |
| 2013/0144231 | A1 | 6/2013 | Hu et al. |
| 2013/0209281 | A1 * | 8/2013 | Locke ............... F04F 7/00 417/63 |
| 2013/0226115 | A1 | 8/2013 | Robinson et al. |
| 2013/0296816 | A1 | 11/2013 | Greener |
| 2013/0304007 | A1 | 11/2013 | Toth |
| 2013/0310809 | A1 | 11/2013 | Armstrong et al. |
| 2014/0088521 | A1 | 3/2014 | Eriksson et al. |
| 2014/0107597 | A1 | 4/2014 | Hu et al. |
| 2014/0171920 | A1 | 6/2014 | Smith et al. |
| 2014/0221907 | A1 | 8/2014 | Scholz et al. |
| 2014/0241922 | A1 * | 8/2014 | Yang ............... F04B 33/00 417/472 |
| 2014/0243767 | A1 | 8/2014 | Hu et al. |
| 2014/0276498 | A1 | 9/2014 | Connor et al. |
| 2014/0343518 | A1 | 11/2014 | Riesinger |

(56) References Cited

U.S. PATENT DOCUMENTS

| | | |
|---|---|---|
| 2015/0005722 A1 | 1/2015 | Hu et al. |
| 2015/0025486 A1 | 1/2015 | Hu et al. |
| 2015/0141941 A1 | 5/2015 | Allen et al. |
| 2015/0148761 A1 | 5/2015 | Hu et al. |
| 2015/0174304 A1 | 6/2015 | Askem et al. |
| 2015/0202354 A1 | 7/2015 | Wall |
| 2015/0217032 A1 | 8/2015 | Allen et al. |
| 2015/0250931 A1 | 9/2015 | Bharti et al. |
| 2016/0045375 A1 | 2/2016 | Zurovcik |
| 2016/0184495 A1 | 6/2016 | Fouillet et al. |
| 2016/0199230 A1 | 7/2016 | Doshi et al. |
| 2016/0206792 A1 | 7/2016 | Worthley |
| 2016/0206793 A1 | 7/2016 | Robinson et al. |
| 2016/0287446 A1 | 10/2016 | Meixner et al. |
| 2016/0361205 A1 | 12/2016 | Mumby et al. |
| 2017/0080133 A1 | 3/2017 | Locke et al. |
| 2017/0112974 A1 | 4/2017 | Fujisaki |
| 2017/0128272 A1 | 5/2017 | Wu et al. |
| 2017/0143552 A1 | 5/2017 | Hartwell et al. |
| 2017/0172806 A1 | 6/2017 | Fung et al. |
| 2017/0181894 A1 | 6/2017 | Allen et al. |
| 2017/0181896 A1 | 6/2017 | Hartwell |
| 2017/0181897 A1 | 6/2017 | Hartwell |
| 2017/0209312 A1 | 7/2017 | Kanchagar et al. |
| 2017/0246113 A1 | 8/2017 | Blaskovich et al. |
| 2017/0266051 A1 | 9/2017 | Hartwell |
| 2017/0367895 A1 | 12/2017 | Holm et al. |
| 2017/0367896 A1 | 12/2017 | Holm et al. |
| 2018/0021178 A1 | 1/2018 | Locke et al. |
| 2018/0133065 A1 | 5/2018 | Hartwell |
| 2018/0140466 A1 | 5/2018 | Hunt |
| 2018/0168869 A1 | 6/2018 | Allen et al. |
| 2018/0221511 A1 | 8/2018 | Ohri et al. |
| 2018/0228482 A1 | 8/2018 | Madsen et al. |
| 2018/0243463 A1 | 8/2018 | Chatterjee et al. |
| 2018/0272052 A1 | 9/2018 | Locke et al. |
| 2018/0303676 A1 | 10/2018 | Bonn |
| 2018/0305468 A1 | 10/2018 | Tramontano et al. |
| 2018/0369460 A1 | 12/2018 | Bonn |
| 2019/0099171 A1 | 4/2019 | Lichty, II et al. |
| 2019/0117575 A1 | 4/2019 | Blaskovich et al. |
| 2019/0183685 A1 | 6/2019 | McNulty et al. |
| 2019/0269835 A1 | 9/2019 | Pinto et al. |
| 2019/0350965 A1 | 11/2019 | Ohri et al. |
| 2020/0000727 A1 | 1/2020 | Blaskovich et al. |
| 2020/0016081 A1 | 1/2020 | Ohri et al. |
| 2020/0069477 A1 | 3/2020 | Holm et al. |
| 2020/0078499 A1 | 3/2020 | Gadde et al. |
| 2020/0085626 A1 | 3/2020 | Braga et al. |
| 2020/0086013 A1 | 3/2020 | Quintanar |
| 2020/0086016 A1 | 3/2020 | Bannister et al. |
| 2020/0093970 A1 | 3/2020 | Hunt et al. |
| 2020/0100945 A1 | 4/2020 | Albert et al. |
| 2020/0101207 A1 | 4/2020 | Weston et al. |
| 2020/0107964 A1 | 4/2020 | Locke et al. |
| 2020/0107967 A1 | 4/2020 | Holm et al. |
| 2020/0108235 A1 | 4/2020 | Locke et al. |
| 2020/0113741 A1 | 4/2020 | Rehbein et al. |
| 2020/0114050 A1 | 4/2020 | Collinson et al. |
| 2020/0114051 A1 | 4/2020 | Pratt et al. |
| 2020/0121509 A1 | 4/2020 | Locke et al. |
| 2020/0121510 A1 | 4/2020 | Hartwell et al. |
| 2020/0121511 A1 | 4/2020 | Locke et al. |
| 2020/0121512 A1 | 4/2020 | Locke et al. |
| 2020/0121833 A9 | 4/2020 | Askem et al. |
| 2020/0129341 A1 | 4/2020 | Coulthard et al. |
| 2020/0129674 A1 | 4/2020 | Moore et al. |
| 2020/0129675 A1 | 4/2020 | Robinson et al. |
| 2020/0155356 A1 | 5/2020 | Greener et al. |

FOREIGN PATENT DOCUMENTS

| | | |
|---|---|---|
| WO | WO 2009/124473 | 10/2009 |
| WO | WO 2010/121186 | 10/2010 |
| WO | WO 2011/162862 | 12/2011 |
| WO | WO 2012/151359 | 11/2012 |
| WO | WO 2014/039557 | 3/2014 |
| WO | WO 2014/145014 | 9/2014 |
| WO | WO 2015/052219 | 4/2015 |
| WO | WO 2017/053384 | 3/2017 |
| WO | WO 2019/113275 | 6/2019 |

OTHER PUBLICATIONS

Blackburn et al., Negative-Pressure Dressings as a Bolster for Skin Grafts, Annals of Plastic Surgery, May 1998, vol. 40, No. 5, 453-457.

Genecov et al., A Controlled Subatmospheric Pressure Dressing Increases the Rate of Skin Graft Donor Site Reepithelialization, Annals of Plastic Surgery, Mar. 1998, vol. 40, No. 3, 219-225.

Molnar et al., Single-Stage Approach to Skin Grafting the Exposed Skull, Jan. 5, 1999, vol. 105, No. 1, 174-177.

Morykwas et al., Vacuum-Assisted Closure: A New Method for Wound Control and Treatment: Animal Studies and Basic Foundation, Annals of Plastic Surgery, Jun. 1997, vol. 38, No. 6, 553-562.

Muensterer et al., A Simple Vacuum Dressing Reduces the Wound Infection Rate of Single-Incision Pediatric Endosurgical Appendectomy, JSLS (2011)15:147-150.

Seifarth et al., A Simple Postoperative Umbilical Negative-Pressure Dressing. Advances in Skin & Wound Care, vol. 26, No. 1 (2013), 26-29.

Sposato et al., Ambulant vacuum-assisted closure of skin-graft dressing in the lower limbs using a portable mini-VAC device. British Journal of Plastic Surgery, (2001), 54, 235-237.

\* cited by examiner

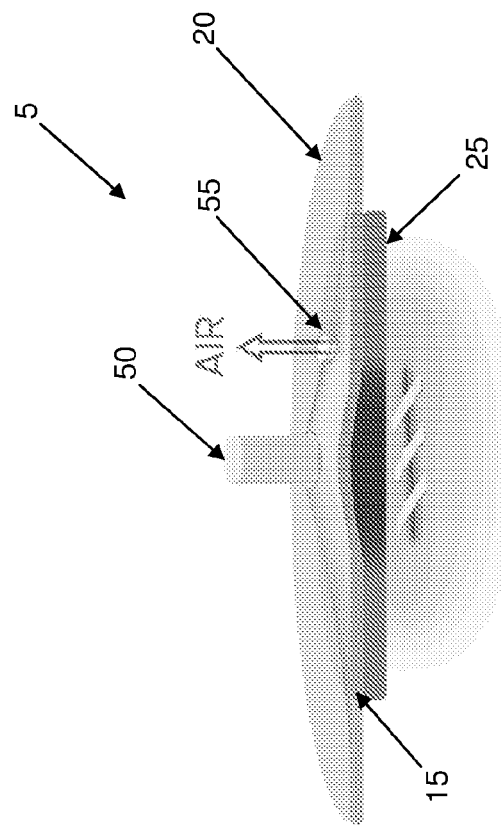
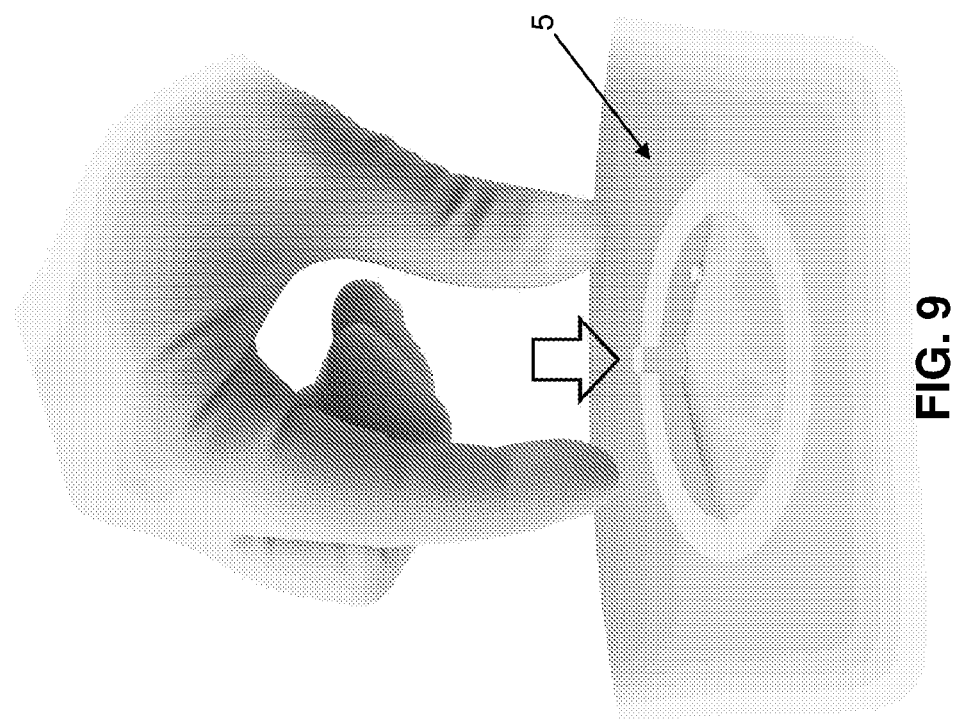
FIG. 9
FIG. 10

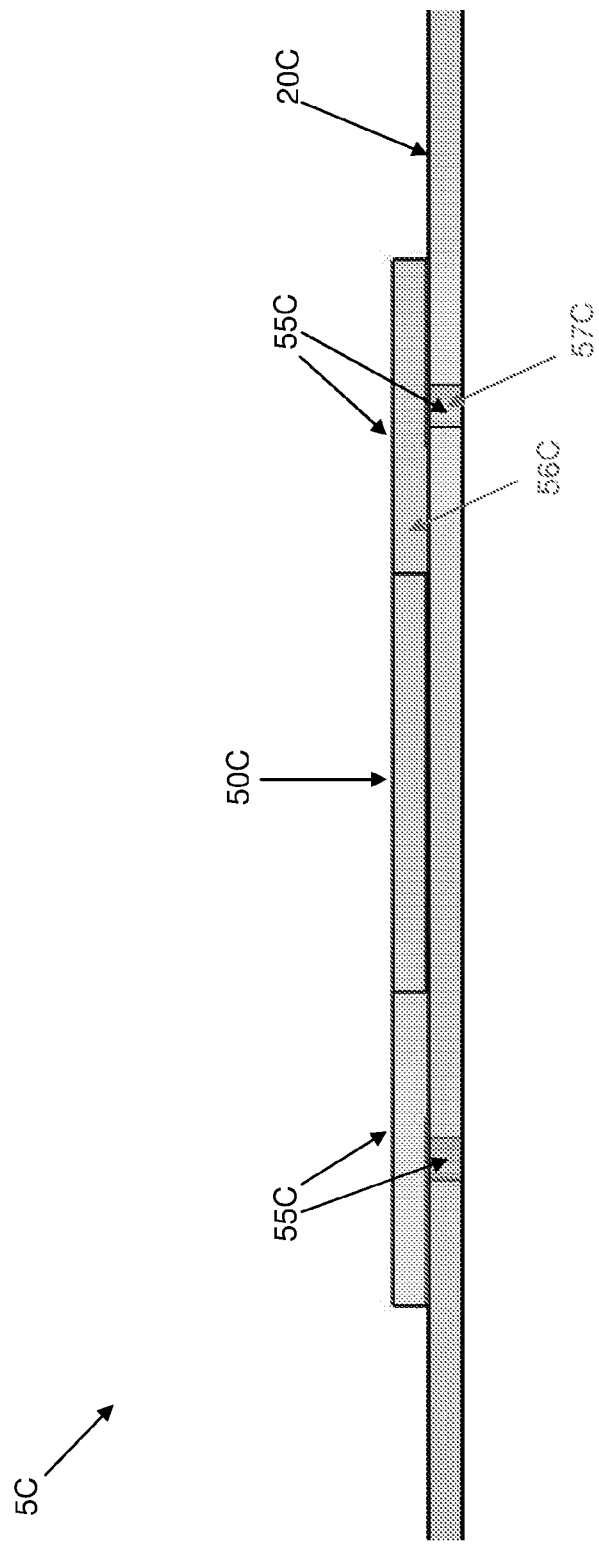

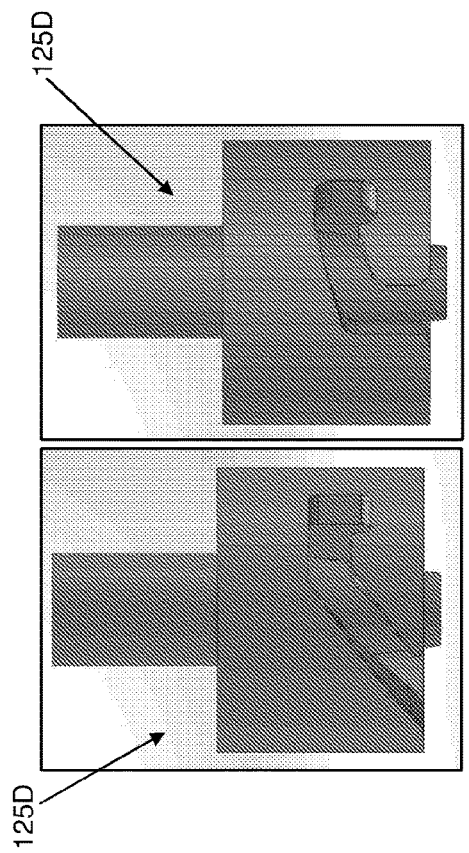
FIG. 25
FIG. 24
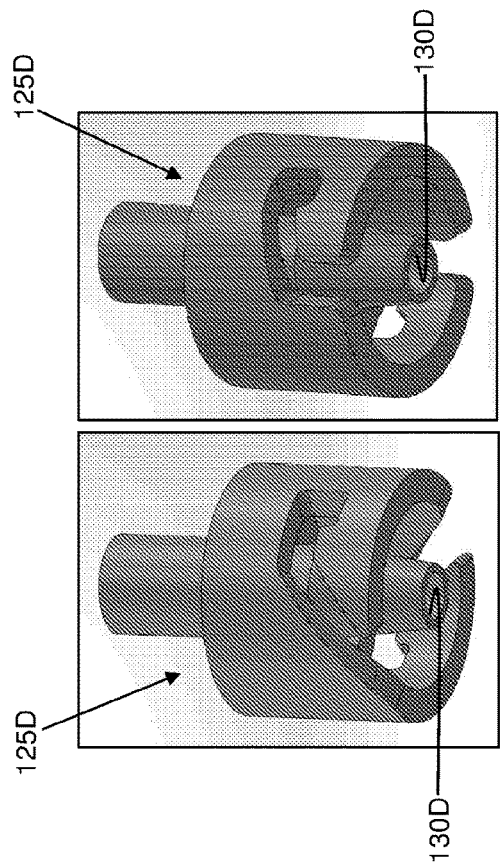
FIG. 23
FIG. 22
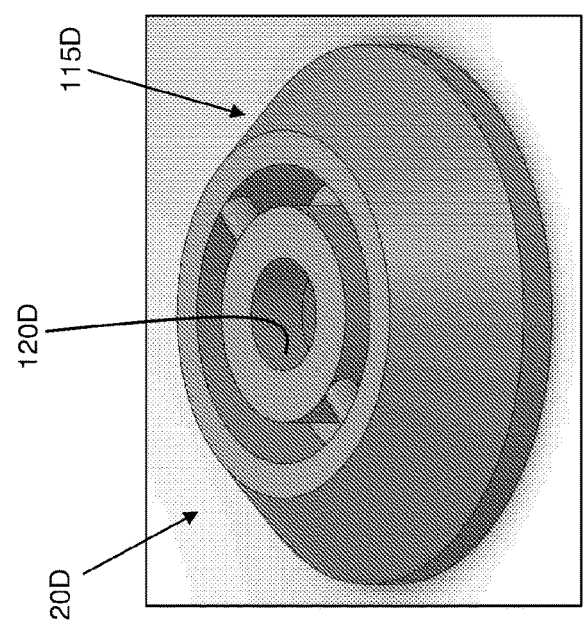
FIG. 21

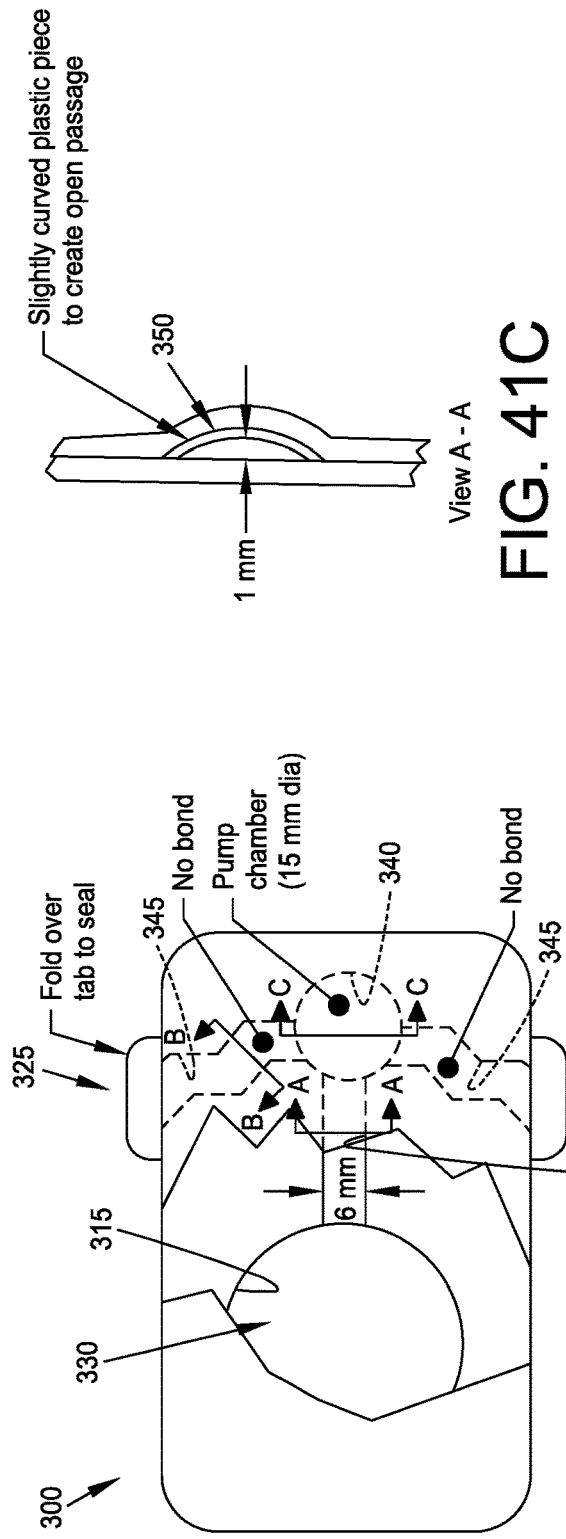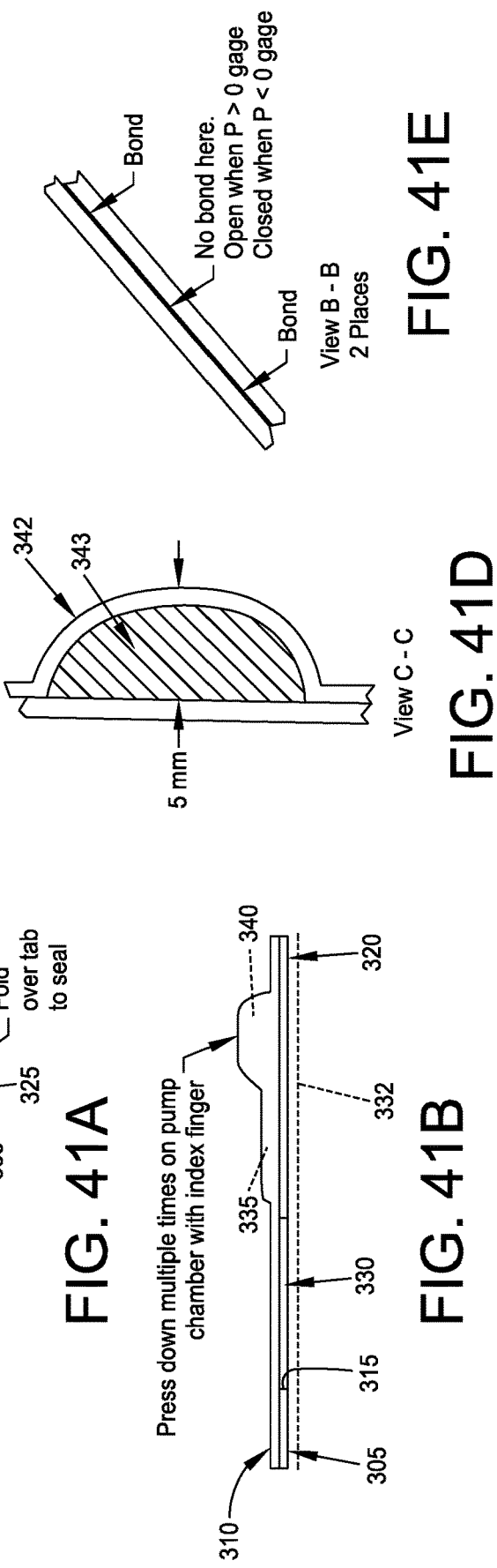

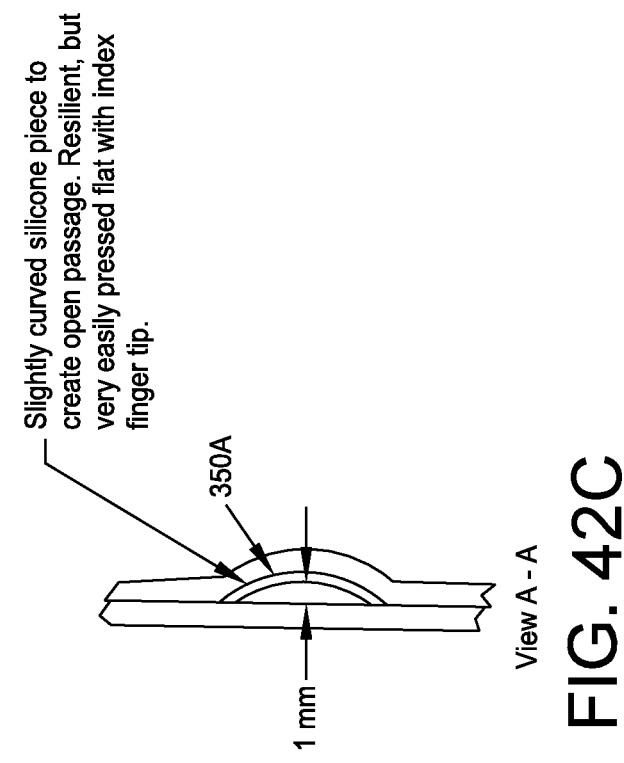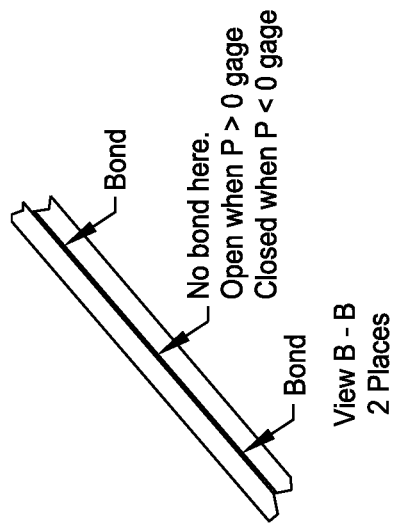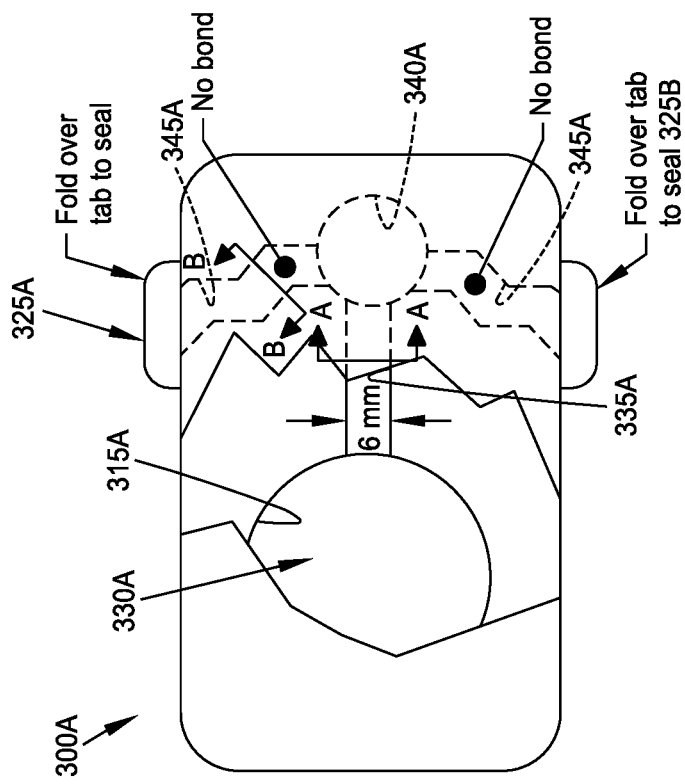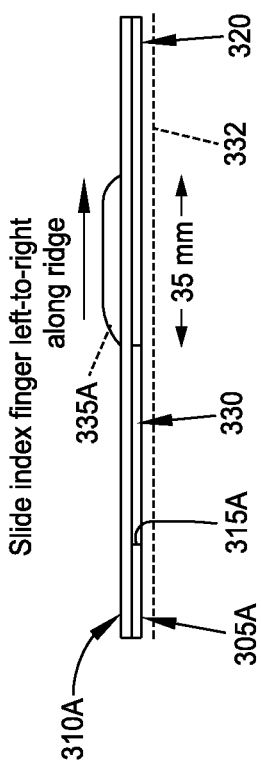
FIG. 42A
FIG. 42B
FIG. 42C
FIG. 42D

MECHANICAL VACUUM DRESSING FOR MECHANICALLY MANAGING, PROTECTING AND SUCTIONING SMALL INCISIONAL WOUNDS

REFERENCE TO PENDING PRIOR PATENT APPLICATION

This patent application claims benefit of prior U.S. Provisional Patent Application Ser. No. 62/462,267, filed Feb. 22, 2017 by Cornell University and Dr. Sang Lee et al. for MECHANICAL VACUUM DRESSING FOR MECHANICALLY MANAGING, PROTECTING AND SUCTIONING SMALL INCISIONAL WOUNDS, which patent application is hereby incorporated herein by reference.

FIELD OF THE INVENTION

This invention relates to wound care in general, and more particularly to wound dressings.

BACKGROUND OF THE INVENTION

Laparoscopic surgery is rapidly becoming the preferred form of surgery for many procedures. Compared to conventional open surgery, laparoscopic surgery is less invasive, requires less recovery time and generally results in fewer complications, including a significantly lower infection rate. In the United States, more than 50% of colectomies are currently performed laparoscopically, as compared to only 10% a decade ago. The trend towards laparoscopic surgery is similar for many other procedures. In all, over 4 million laparoscopic surgeries are performed annually in the United States.

Laparoscopic surgery patients typically have 1 to 4 small (e.g., 0.5" to 1" long), "full thickness" incisions (see FIG. 1) that generally need to be treated for a period of 1-2 days. Surgical Site Infections (SSIs) remain a major concern for medical personnel. SSIs can result in longer hospitalization times, increased morbidity, increased mortality, and potential reputational and financial consequences to healthcare institutions and medical personnel.

Under the current standard of care, laparoscopic wounds are typically passively managed using standard "basic care" practices regardless of the wound complexity (e.g., non-healing wounds, fistulas, infections, etc.). These standard "basic care" practices generally involve closing the wound using surgical sutures, staples or glue. The wound is then left unprotected or is dressed, e.g., using "4×4 gauze" dressings. As a result, the wounds are often unprotected from physical damage (e.g., from the patient moving about or from external impact). In addition, with "4×4 gauze" dressings, there is no effective way to actively remove exudates from weeping wounds—at best, the "4×4 gauze" dressings might wick exudates away from the wound, but they do not actively pull exudates from the wound.

Negative pressure wound therapy (NPWT) has been used for many years to accelerate the healing of complicated, non-healing wounds after open surgery. The key element of a NPWT system involves applying suction to a fully-sealed absorbent dressing over a period of days or weeks. The NPWT system works by bringing the wound edges closer together to re-establish tissue integrity, draining wound exudates, increasing blood flow, decreasing inflammation and improving wound biochemistry. A number of publications also indicate that NPWT may work to reduce SSIs in high-risk patients.

No commercially-available NPWT system currently exists which is specifically designed to treat laparoscopic wounds. Commercially-available NPWT systems currently utilize either electrically-powered suction pumps or have an additional vacuum canister that is attached to the patient. Commercially-available NPWT systems are typically bulky, expensive (e.g., units typically range in price from about $400 to about $2000), and skill-intensive and time-intensive in use. Commercially-available NPWT systems have generally been limited to use only as a "last resort" in severe cases, and have generally only been used with large wounds generated during open surgery.

Thus there is a need for a novel NPWT system that is designed for use with smaller incisional wounds (including laparoscopic incisional wounds) which typically heal much faster than larger open wounds and which could benefit from the use of a smaller, simpler and less expensive NPWT system to support wound healing on a prophylactic basis.

SUMMARY OF THE INVENTION

The present invention comprises the provision and use of a novel NPWT system that is designed for use with smaller incisional wounds (including laparoscopic incisional wounds) which typically heal much faster than larger open wounds and which could benefit from the use of a smaller, simpler and less expensive NPWT system to support wound healing on a prophylactic basis.

More particularly, the present invention comprises a small, simple, and inexpensive mechanical vacuum dressing which uses compressive and suctioning forces to treat small, closed surgical incisional wounds that may be draining wounds, including laparoscopic surgical incisional wounds.

The novel mechanical vacuum dressing facilitates wound treatment by:

(1) mechanically drawing the wound edges together so as to re-establish tissue integrity;

(2) providing a protective healing environment that is occlusive to external air and liquids; and (3) actively removing exudates from the wound.

The present invention is a fully-mechanical (e.g., non-electrical) NPWT device, with an integrated vacuum pump, and has a small, simple, and inexpensive construction which allows for its use prophylactically on patients with small incisional wounds (e.g., laparoscopic patients).

In general, the present invention is a multi-layered integrated device which comprises a base for releasable fixation to the tissue surrounding the wound, an absorptive material (e.g., gauze, foam, hydrogel, etc.) carried by the base and configured to contact the wound and receive exudates from the wound, an outer occlusive layer connected to the base for sealing the wound, and mechanical suction means for evacuating the area between the absorptive material and the outer occlusive layer so as to establish a negative pressure to draw the edges of the wound together and to pull exudates from the wound. The components of the mechanical vacuum dressing are secured together so as to make a single integrated unit which is attached to the skin of the patient about the periphery of the wound via adhesive.

The absorptive material of the mechanical vacuum dressing may be embedded with antimicrobials, growth factors and/or other healing agents so as to enhance healing. By way of example but not limitation, the absorptive material of the mechanical vacuum dressing may be embedded with microstructures to signal cell proliferation and cell migration.

In one preferred form of the invention, there is provided a mechanical vacuum dressing comprising:

a first valve layer comprising a first one-way valve;
a second valve layer comprising a second one-way valve;
the first valve layer being joined to the second valve layer so as to define a chamber therebetween;
the first one-way valve being configured to admit fluid into the chamber through the first one-way valve but prevent fluid from exiting the chamber through the first one-way valve;
the second one-way valve being configured to exhaust fluid from the chamber through the second one-way valve but prevent fluid from entering the chamber through the second one-way valve; and
the second valve layer comprising an elastomeric material such that (i) when the second valve layer is moved away from the first valve layer, the volume of the chamber is increased, and (ii) when the second valve layer is thereafter released, the second valve layer moves back towards the first valve layer and the volume of the chamber is decreased.

In another preferred form of the invention, there is provided a method for providing negative pressure wound therapy (NPWT), the method comprising:
providing a mechanical vacuum dressing comprising:
a first valve layer comprising a first one-way valve;
a second valve layer comprising a second one-way valve;
the first valve layer being joined to the second valve layer so as to define a chamber therebetween;
the first one-way valve being configured to admit fluid into the chamber through the first one-way valve but prevent fluid from exiting the chamber through the first one-way valve;
the second one-way valve being configured to exhaust fluid from the chamber through the second one-way valve but prevent fluid from entering the chamber through the second one-way valve; and
the second valve layer comprising an elastomeric material such that (i) when the second valve layer is pulled away from the first valve layer, the volume of the chamber is increased, and (ii) when the second valve layer is thereafter released, the second valve layer moves back towards the first valve layer and the volume of the chamber is decreased;
positioning the mechanical vacuum dressing at a wound site so that the first one-way valve is in communication with the wound site;
moving the second valve layer away from the first valve layer so as to increase the volume of the chamber and apply suction to the wound site; and
releasing the second valve layer so that the volume of the chamber is decreased.

In another preferred form of the invention, there is provided a mechanical vacuum dressing comprising:
a base for releasable fixation to tissue surrounding a wound;
absorptive material carried by the base and configured to contact the wound and receive exudates from the wound;
an outer occlusive layer connected to the base for sealing the wound; and
a peristaltic pump for evacuating the area between the absorptive material and the outer occlusive layer so as to pull exudates from the wound.

In another preferred form of the invention, there is provided a method for providing negative pressure wound therapy (NPWT), the method comprising:
providing a mechanical vacuum dressing comprising:
a base for releasable fixation to tissue surrounding a wound;
absorptive material carried by the base and configured to contact the wound and receive exudates from the wound;
an outer occlusive layer connected to the base for sealing the wound; and
a peristaltic pump for evacuating the area between the absorptive material and the outer occlusive layer so as to pull exudates from the wound;
positioning the mechanical vacuum dressing against tissue so that the absorptive material carried by the base contacts the wound; and
using the peristaltic pump to provide suction to the area between the absorptive material and the outer occlusive layer so as to pull exudates from the wound.

In another preferred form of the invention, there is provided a mechanical vacuum dressing comprising:
a base for releasable fixation to tissue surrounding a wound;
absorptive material carried by the base and configured to contact the wound and receive exudates from the wound; and
an outer occlusive layer connected to the base for sealing the wound;
wherein the outer occlusive layer comprises a resilient dome defining a chamber in communication with the wound, and further wherein the outer occlusive layer is selectively bonded to the base so as to form a passageway which (i) is open when the pressure within the chamber is above a pre-determined threshold, and (ii) is closed when the pressure within the chamber is below a pre-determined threshold.

In another preferred form of the invention, there is provided a method for providing negative pressure wound therapy (NPWT), the method comprising:
providing a mechanical vacuum dressing comprising:
a base for releasable fixation to tissue surrounding a wound;
absorptive material carried by the base and configured to contact the wound and receive exudates from the wound; and
an outer occlusive layer connected to the base for sealing the wound;
wherein the outer occlusive layer comprises a resilient dome defining a chamber in communication with the wound, and further wherein the outer occlusive layer is selectively bonded to the base so as to form a passageway which (i) is open when the pressure within the chamber is above a pre-determined threshold, and (ii) is closed when the pressure within the chamber is below a pre-determined threshold;
positioning the mechanical vacuum dressing against tissue so that the absorptive material carried by the base contacts the wound; and
compressing and releasing the resilient dome so as to provide suction to the area between the absorptive material and the outer occlusive layer so as to pull exudates from the wound.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 4-10 are schematic views showing operation of the novel mechanical vacuum dressing of FIGS. 2 and 3;

FIGS. 14A-14C are schematic views showing yet another novel mechanical vacuum dressing formed in accordance with the present invention;

FIGS. 21-25 are schematic views showing other alternative connection mechanisms for the novel mechanical vacuum dressing of FIG. 15;

FIGS. 41A-41E are schematic views showing another novel mechanical vacuum dressing formed in accordance with the present invention; and FIGS. 42A-42D are schematic views showing still another novel mechanical vacuum dressing formed in accordance with the present invention.

DETAILED DESCRIPTION OF THE PREFERRED EMBODIMENTS

Pull Tab Mechanical Vacuum Dressing

Figure 1:
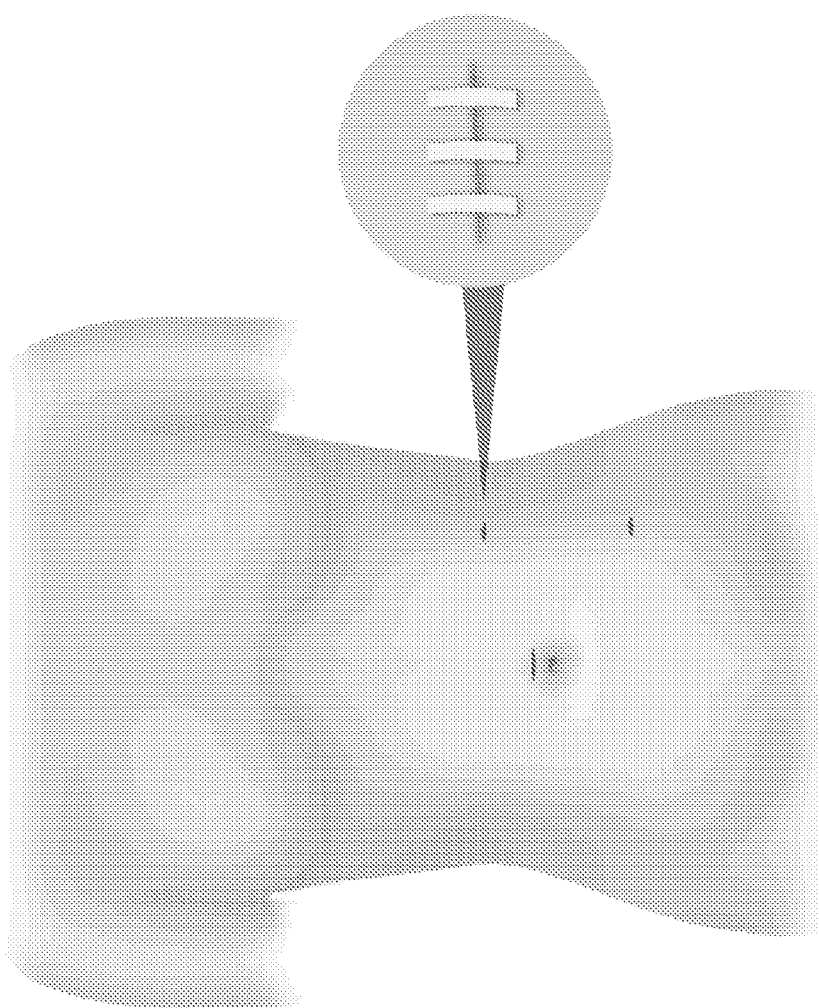
FIG. 1 is a schematic view showing a plurality of laparoscopic incisions in the torso of a patient.
Figure 2:
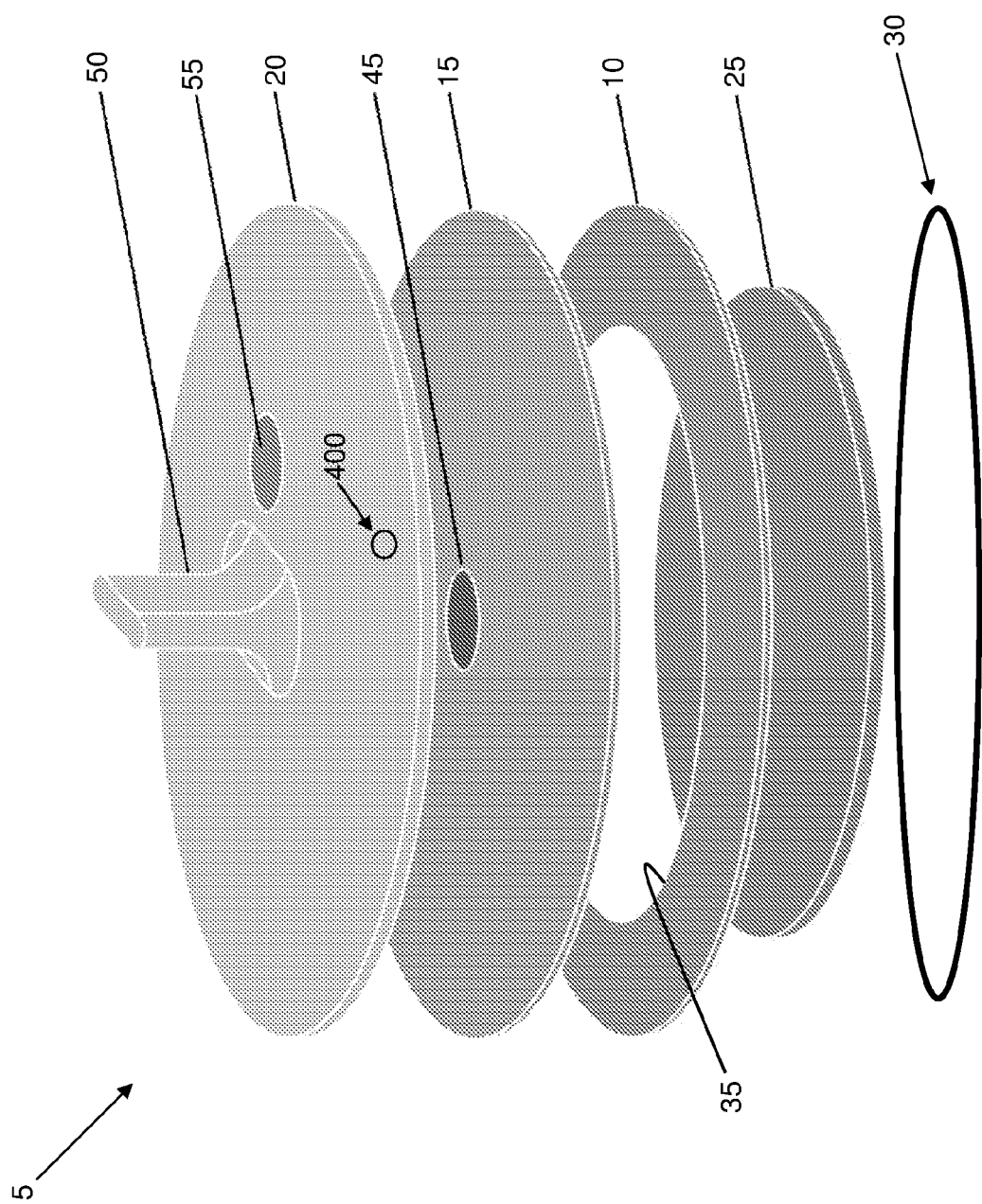
FIGS. 2 and 3 are schematic views showing a novel mechanical vacuum dressing formed in accordance with the present invention.
Figure 3:
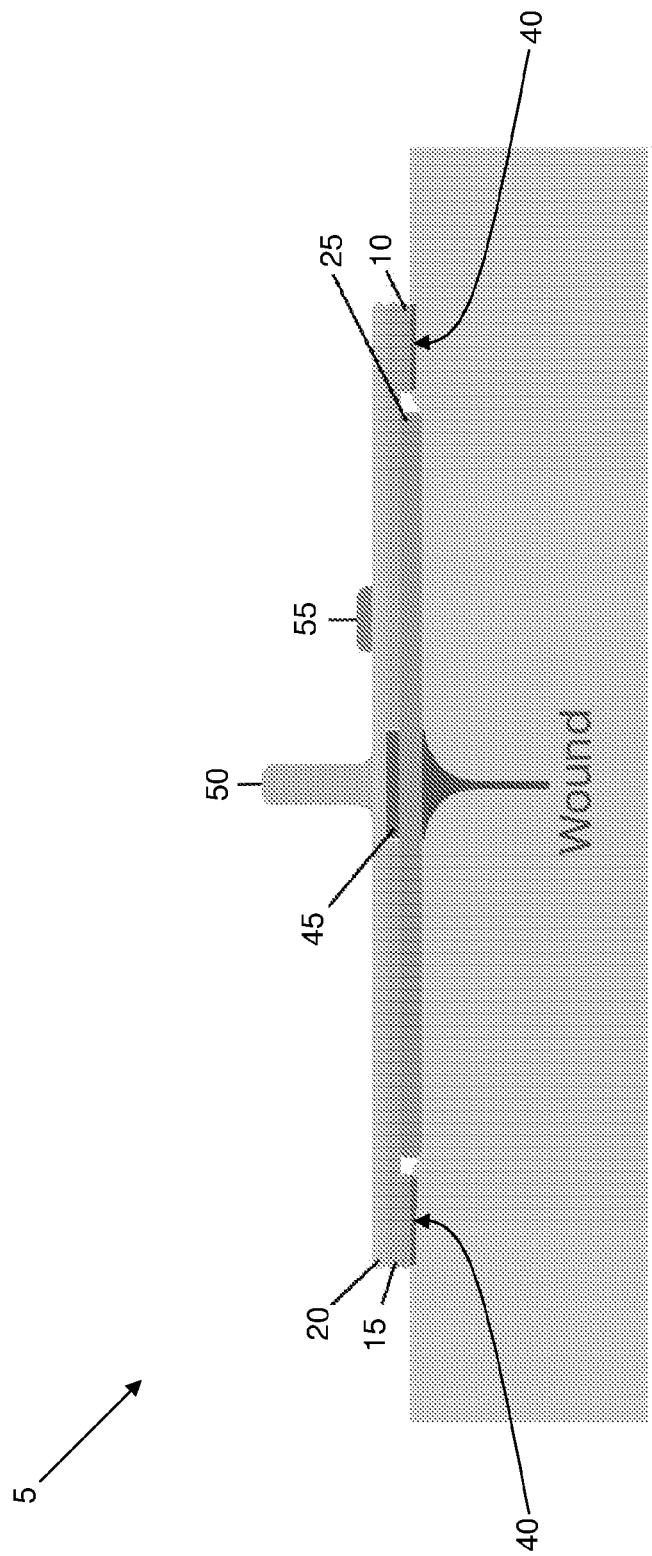
Figure 4:
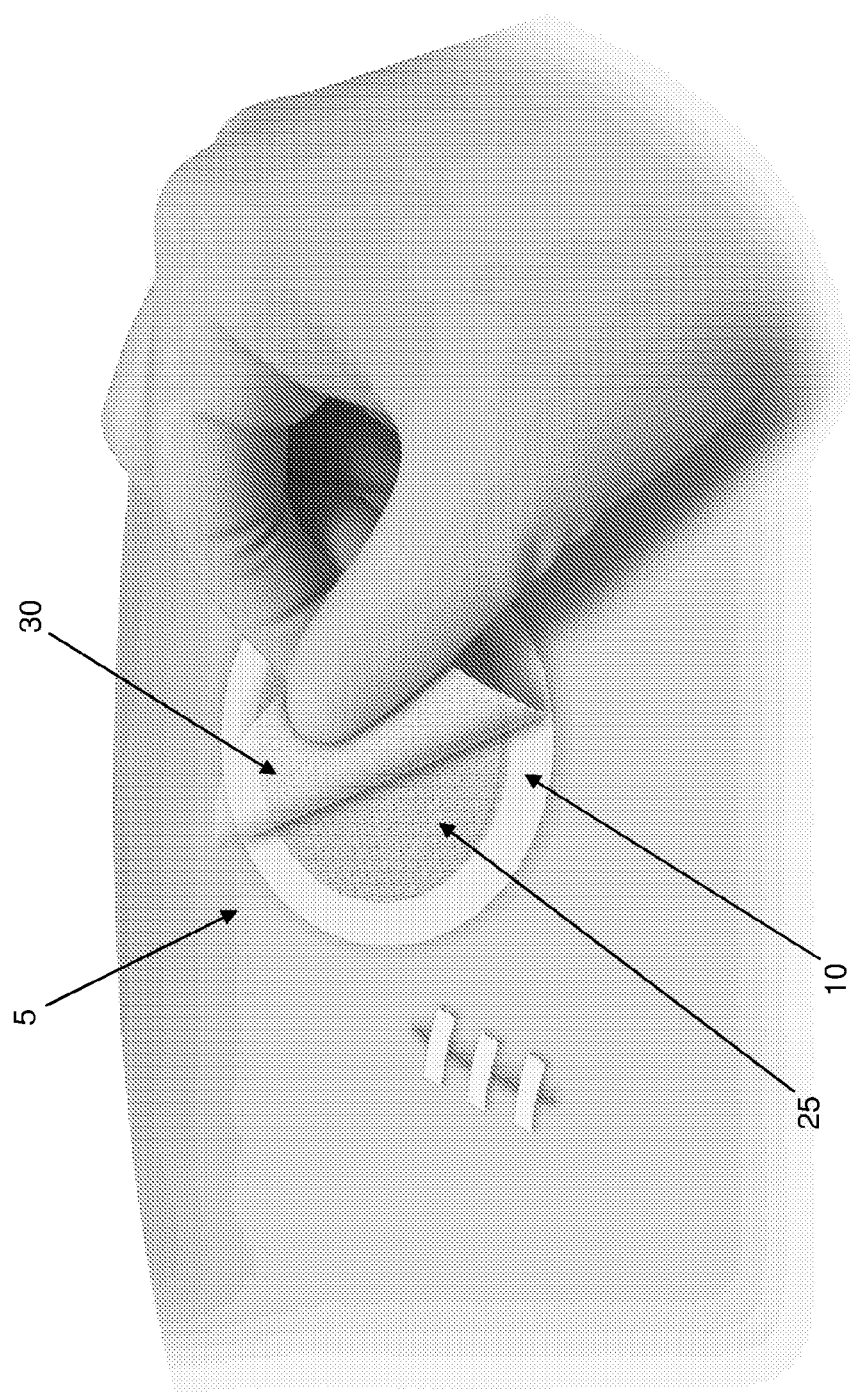
Figure 5:
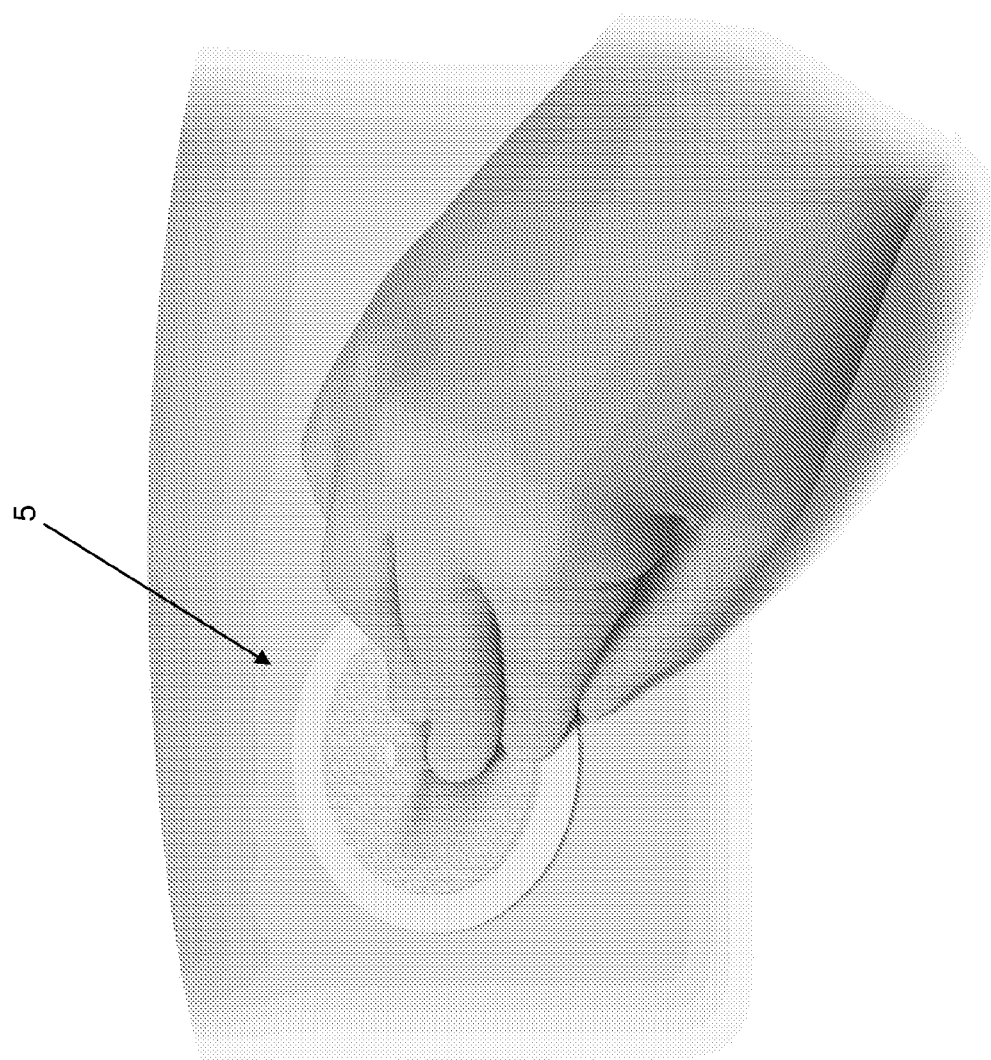
Figure 6:
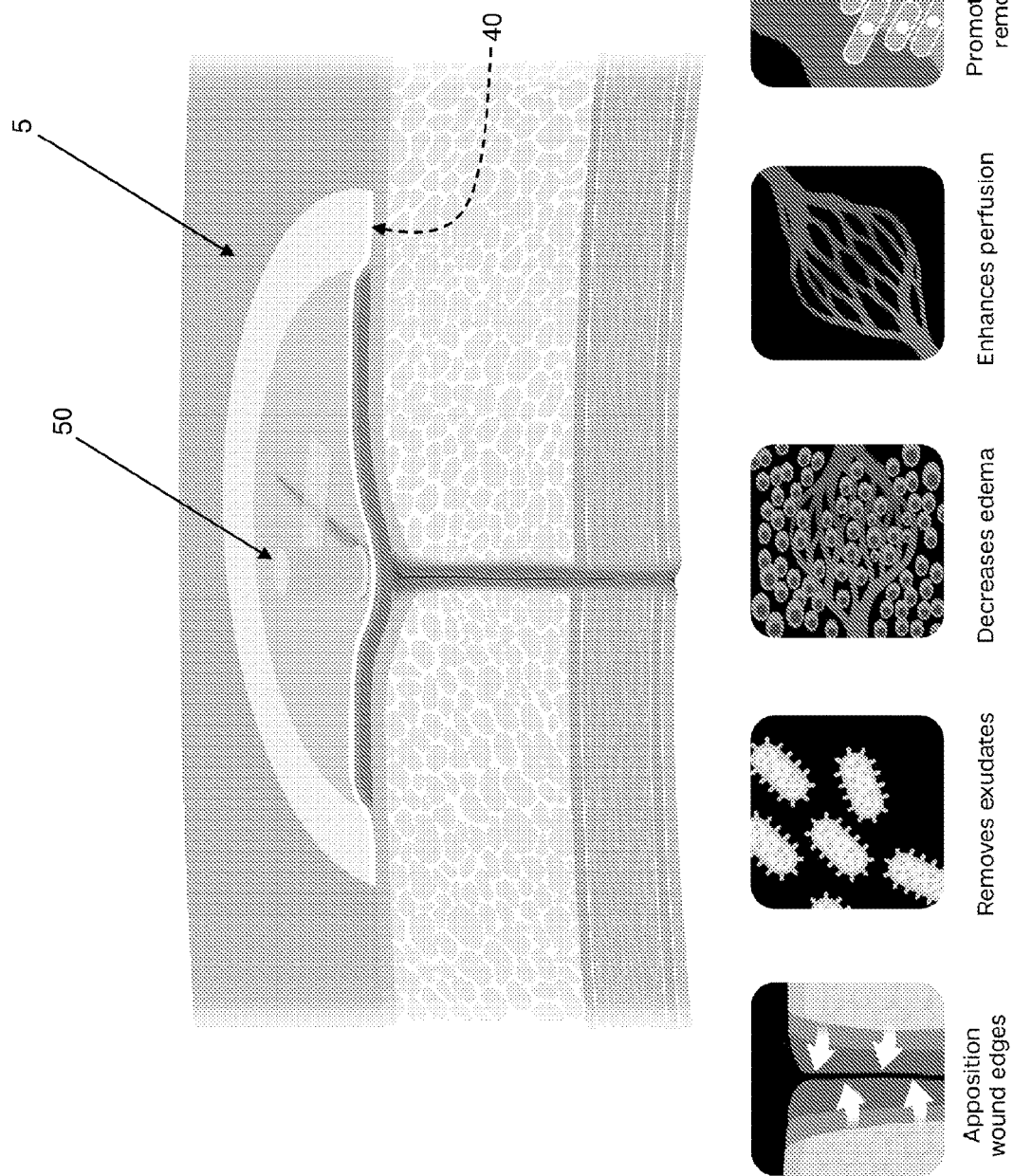

Looking first at FIGS. 2 and 3, there is shown a novel mechanical vacuum dressing 5 formed in accordance with the present invention. Novel mechanical vacuum dressing 5 generally comprises an adhesive layer 10, an internal valve layer 15, an external valve layer 20, an absorbent dressing 25 and a release liner 30, all secured to one another so as to form a singular mechanical vacuum dressing. As seen in FIG. 2, internal valve layer 15 is sandwiched between adhesive layer 10 and external valve layer 20. Absorbent dressing 25 is disposed against internal valve layer 15. Release liner 30 is disposed against adhesive layer 10 and absorbent dressing 25.

Adhesive layer 10 generally comprises a flexible material having a central opening 35. Adhesive layer 10 is sized so that the perimeter of central opening 35 can circumscribe a wound. Adhesive 40 (FIG. 3) is carried by the bottom surface of adhesive layer 10. Adhesive layer 10 is constructed so that adhesive layer 10 can form an airtight seal with the skin of a patient. In one preferred form of the invention, absorbent dressing 25 is received within central opening 35 of adhesive layer 10.

Internal valve layer 15 comprises a flexible material having an internal one-way valve 45. Internal one-way valve 45 may be substantially any one-way valve of the sort well known in the valve art. Internal valve layer 15 is sized so as to be substantially the same size as, or larger than, central opening 35 in adhesive layer 10.

It will be appreciated that internal one-way valve 45 of internal valve layer 15 permits fluid (e.g., gases and liquids) to flow from absorbent dressing 25 into the region above internal valve layer 15 but prevents fluid from flowing from the region above internal valve layer 15 back to absorbent dressing 25.

Absorbent dressing 25 is preferably formed out of a fluid-permeable, absorptive flexible material, e.g., a woven or non-woven dressing, a foam dressing, etc. In one preferred form of the invention, absorbent dressing 25 is formed out of a hyper-absorptive material, e.g., a hydrophilic foam.

Figure 7:
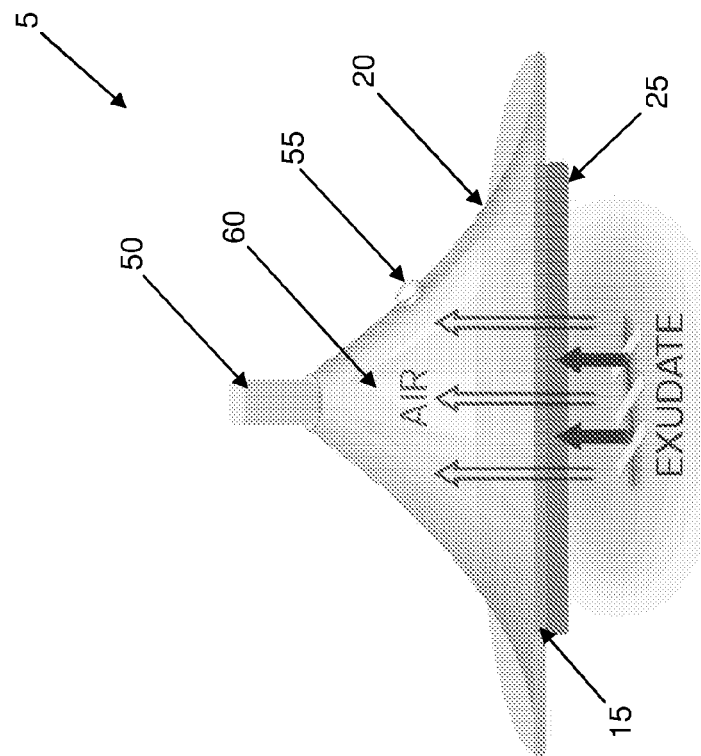
Figure 8:
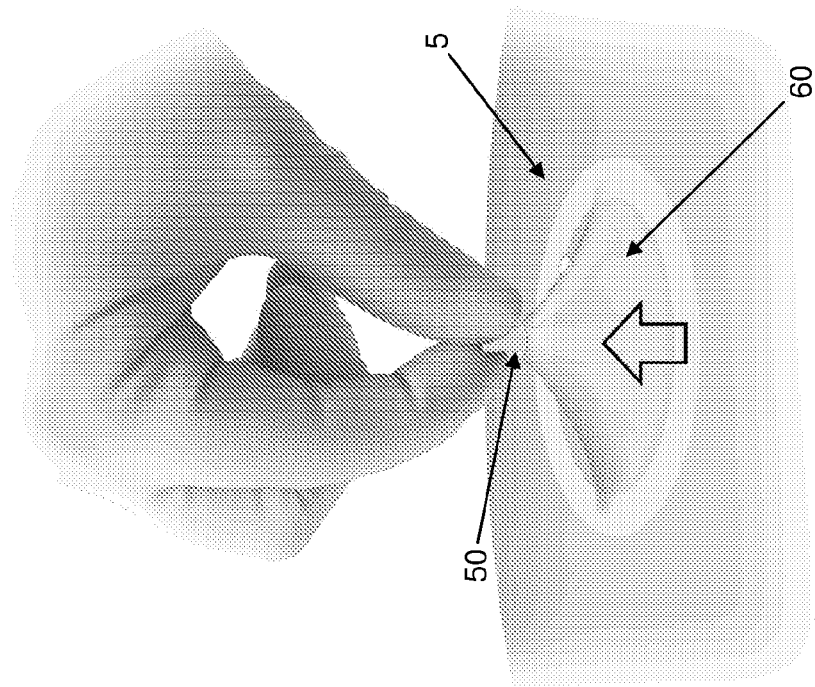

External valve layer 20 generally comprises a pull tab 50 and an external one-way valve 55. External one-way valve 55 may be substantially any one-way valve of the sort well known in the valve art. External valve layer 20 is formed out of an elastomeric material such that (i) by pulling upward on pull tab 50, a chamber 60 (see FIGS. 7 and 8) can be created between external valve layer 20 and internal valve layer 15, whereby to create a negative pressure within chamber 60, and (ii) when pull tab 50 is released, elastomeric external valve layer 20 will return to its original configuration, whereby to minimize chamber 60.

It will be appreciated that external one-way valve 55 of external valve layer 20 permits fluid (e.g., gases and liquids) to flow from the region below external valve layer 20 into the region above external valve layer 20 but prevents fluid from flowing from the region above external valve layer 20 to the region below external valve layer 20.

Thus it will be appreciated that internal one-way valve 45 is configured to allow fluid from the wound site to pass into chamber 60 when external valve layer 20 is pulled upward, so as to expand chamber 60, but to prevent fluid in chamber 60 from passing to the wound site when external valve layer 20 is released. And it will be appreciated that external one-way valve 55 is configured to prevent fluid in the region above external valve layer 20 from entering chamber 60 through external one-way valve 55 when elastomeric external valve layer 20 is pulled upward so as to expand chamber 60, but to pass fluid from chamber 60 to the region outside mechanical vacuum dressing 5 when external valve layer 20 is released (and elastomeric external valve layer 20 returns to its original configuration).

In one preferred form of the invention, internal one-way valve 45 is configured to allow air from the wound site to enter chamber 60 but to prevent air in chamber 60 from passing back to the wound site, and external one-way valve 55 is configured to pass air from chamber 60 to the region outside mechanical vacuum dressing 5 but to prevent air from the region above external valve layer 20 from passing into chamber 60 through external one-way valve 55.

If desired, a removable frame (not shown) may be provided about the periphery of adhesive layer 10 so as to facilitate moving mechanical vacuum dressing 5 to the wound site and adhering the mechanical vacuum dressing to the skin of the patient. Then, after the mechanical vacuum dressing has been adhered to the skin of the patient, the removable frame (not shown) may be removed, leaving the mechanical vacuum dressing adhered to the skin of the patient. By way of example but not limitation, the removable frame (not shown) may be connected to the periphery of adhesive layer 10 by a perforation line, a score line, tabs, etc. It should be appreciated that the connection between the removable frame (not shown) and the periphery of adhesive layer 10 is sufficiently robust that mechanical vacuum dressing 5 can be manipulated by means of the removable frame (not shown), but is easily severable upon demand so that the removable frame (not shown) can be separated from mechanical vacuum dressing 5 after mechanical vacuum dressing 5 has been secured to the skin of a patient. Preferably, the removable frame (not shown) does not have an adhesive on its underside, so that the removable frame (not shown) comes away easily from the skin of the patient once adhesive layer 10 of mechanical vacuum dressing 5 has been adhered to the skin of the patient.

Looking now at FIGS. 4-11, mechanical vacuum dressing 5 is intended to be used as follows. First, release liner 30 is removed from the bottom surface of absorbent dressing 25 and adhesive layer 10 (see FIG. 4). Then mechanical vacuum dressing 5 is positioned against the skin of the patient so that absorbent dressing 25 is positioned against the wound, with adhesive 40 securing mechanical vacuum dressing 5 to the skin of the patient, thereby forming an airtight seal with the skin of the patient, mechanically holding the wound edges together so as to re-establish tissue integrity, and with mechanical vacuum dressing 5 providing a protective healing environment that is occlusive to external air and liquids (see FIGS. 5 and 6). Next, pull tab 50 is pulled upward, tenting elastomeric external valve layer 20 (see FIGS. 7 and 8) and, by virtue of such tenting, creating suction within chamber 60. As this suction is created, adhesive layer 10 flexes and the edges of the wound are drawn together, and internal one-way valve 45 opens and air from the wound site is actively drawn up into chamber 60 and exudate from the wound is actively drawn into absorbent dressing 25. Pull tab 50 is then released, allowing the elastomeric material of external valve layer 20 to return back to its previous configuration, with fluid within chamber 60 being vented out external one-way valve 55 (see FIGS. 9 and 10). It should be appreciated that the fluid vented out external one-way valve 55 is substantially all air, with the liquid from the wound being absorbed by the absorbent dressing 25. Note that none of the fluid contained within chamber 60 is vented back to the wound site due to the presence and function of internal one-way valve 45.

Significantly, by virtue of the airtight seal of adhesive layer 10 against the skin of the patient, internal one-way valve 45 and external one-way valve 55, the suction created within chamber 60 will continue to be applied to the wound even after pull tab 50 has been released, mechanically holding the wound edges together and continuing to draw exudate out of the wound and into absorbent dressing 25.

It will be appreciated that pull tab 50 may be pulled and released multiple times in order to establish the desired level of suction at the wound site.

Thereafter, whenever it is desired to re-establish negative pressure within chamber 60 (e.g., because of suction/leakage), pull tab 50 is again grasped, pulled upward and released.

It is anticipated that multiple cycles of pulling suction within chamber 60 may be used, e.g., one cycle after the other to initially establish the desired suction within chamber 60, or thereafter periodically re-cycling so as to re-establish the desired negative pressure within chamber 60.

After 1-2 days, mechanical vacuum dressing 5 may be removed from the wound.

Figure 11:
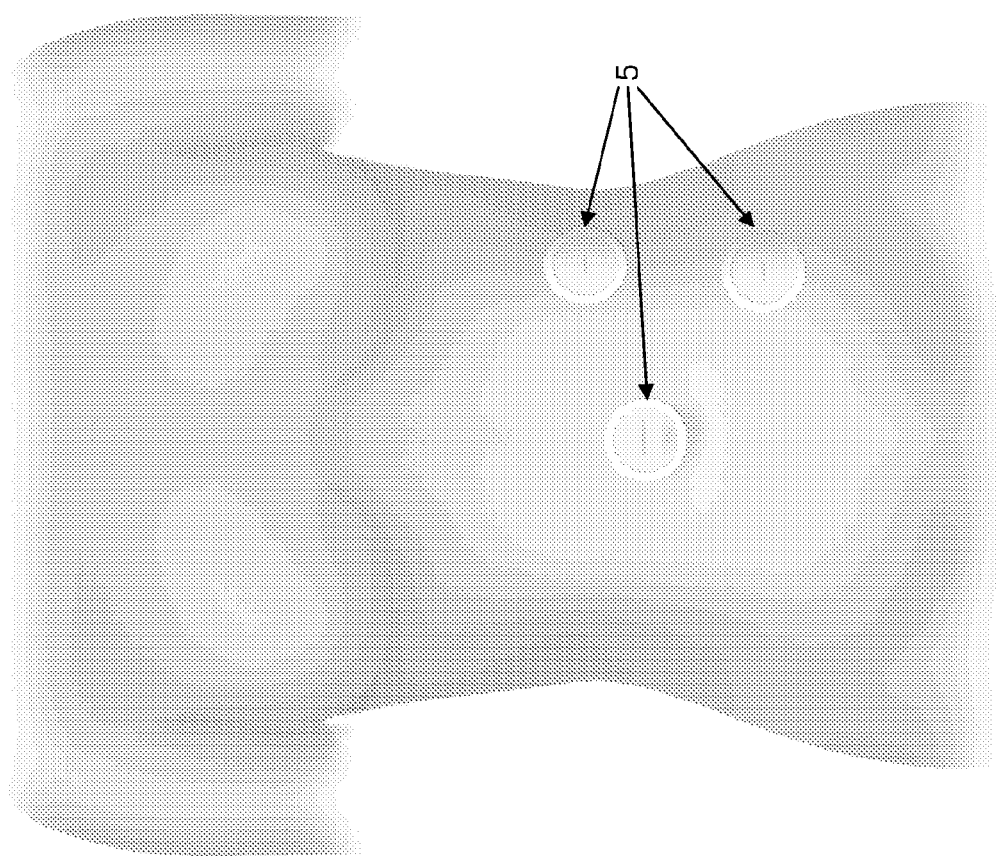
FIG. 11 is a schematic view showing a plurality of the mechanical vacuum dressings of FIGS. 2 and 3 covering laparoscopic incisions in the torso of a patient.

FIG. 11 shows multiple mechanical vacuum dressings 5 applied to the torso of a patient. Note that when external valve layer 20 has returned to its unbiased condition (i.e., when pull tab 50 is not being pulled so as to tent external valve layer 20 away from adhesive layer 10), mechanical vacuum dressing 5 has a relatively low profile configuration which does not intrude on patient activities.

Thus it will be seen that mechanical vacuum dressing 5 may be used to mechanically draw the wound edges together so as to re-establish tissue integrity, provide a protective healing environment that is occlusive to external air and liquids, and actively remove exudates from the wound.

Figure 12:
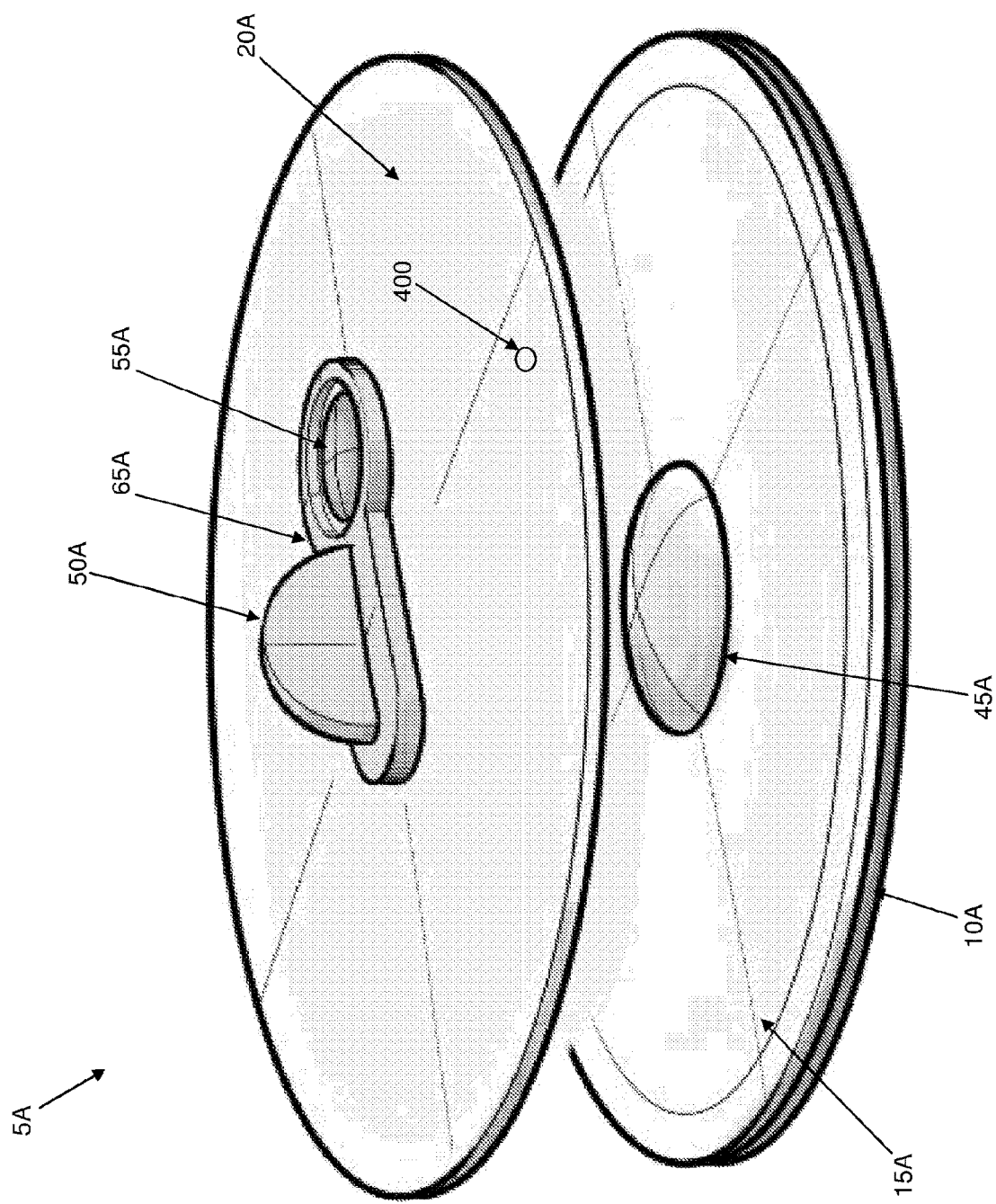
FIG. 12 is a schematic view showing another novel mechanical vacuum dressing formed in accordance with the present invention.

Mechanical Vacuum Dressing wherein the Pull Tab and the External One-Way Valve are Integrated Into a Single Subassembly Looking next at FIG. 12, there is shown another mechanical vacuum dressing 5A formed in accordance with the present invention. Mechanical vacuum dressing 5A is generally similar to mechanical vacuum dressing 5 described above, except that the aforementioned pull tab 50 and the aforementioned external one-way valve 55 are integrated into a single subassembly 65A which is mounted to external valve layer 20A.

In use, when pull tab 50A is pulled upward, external valve layer 20A is tented above internal valve layer 15A, creating suction within the chamber (not shown in FIG. 12) which is disposed between the tented external valve layer 20A and the underlying internal valve layer 15A. As this suction is created, adhesive layer 10A flexes and the edges of the wound are drawn together, internal one-way valve 45A opens, air from the wound site is actively drawn into the chamber which is disposed between the tented external valve layer 20A and the underlying internal valve layer 15A, and exudate from the wound is actively drawn into the absorbent dressing (not shown in FIG. 12) disposed beneath interval valve layer 15A. When pull tab 50A is released, the elastomeric material of external valve layer 20A causes external valve layer 20A to return back to its previous configuration, with air within the chamber (which is disposed between the tented external valve layer 20A and the underlying internal valve layer 15A) being vented out external one-way valve 55A.

Significantly, by virtue of the airtight seal of adhesive layer 10A against the skin of the patient, internal one-way valve 45A and external one-way valve 55A, the suction created within the chamber (which is disposed between the tented external valve layer 20A and the underlying internal valve layer 15A) will continue to be applied to the wound even after pull tab 50A has been released, mechanically holding the wound edges together and continuing to draw exudate out of the wound and into the absorbent dressing (not shown in FIG. 12) disposed beneath interval valve layer 15A.

Streamlined Mechanical Vacuum Dressing

Figure 13:
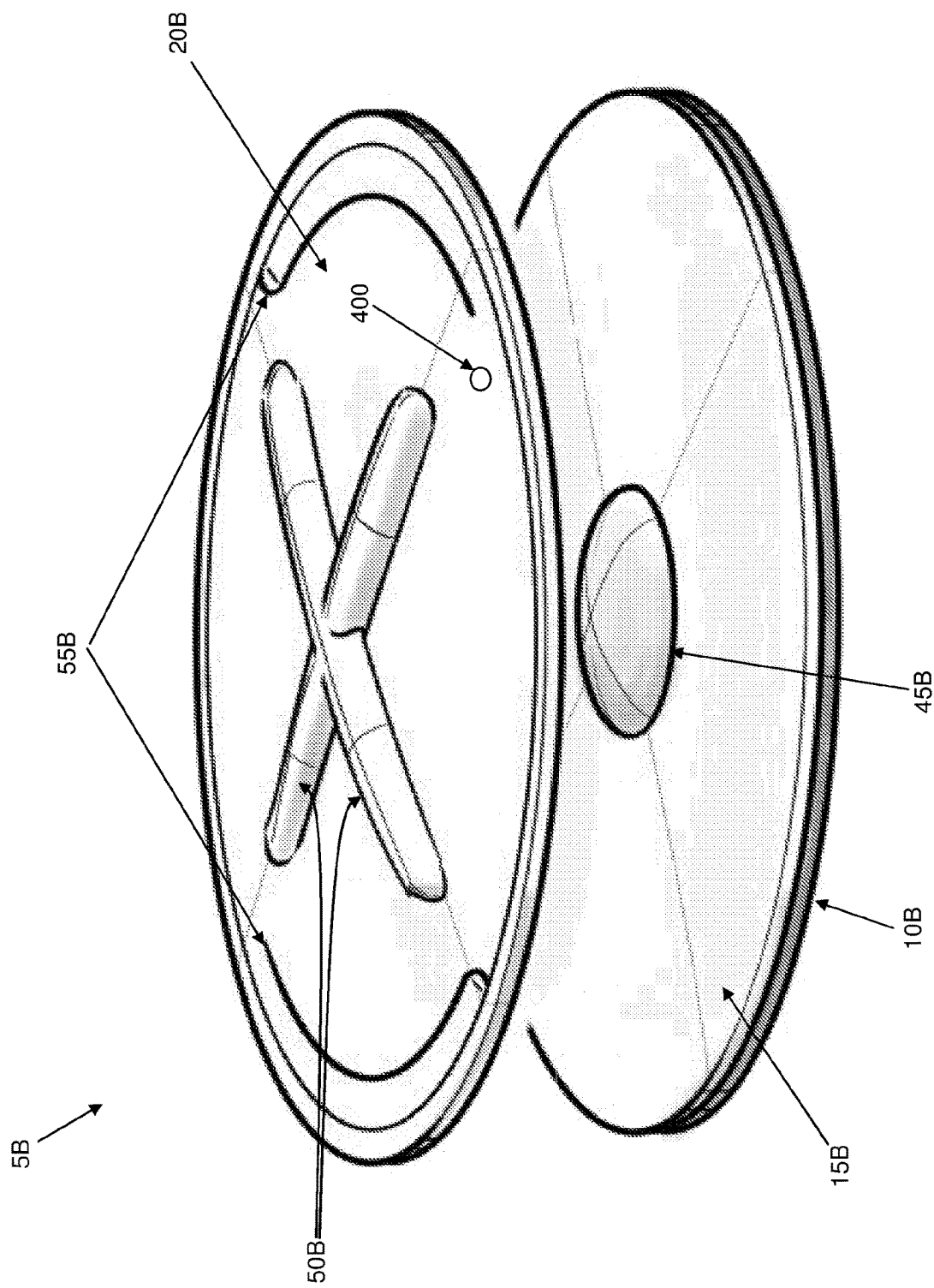
FIGS. 13 and 14 are schematic views showing still another novel mechanical vacuum dressing formed in accordance with the present invention.
Figure 14:
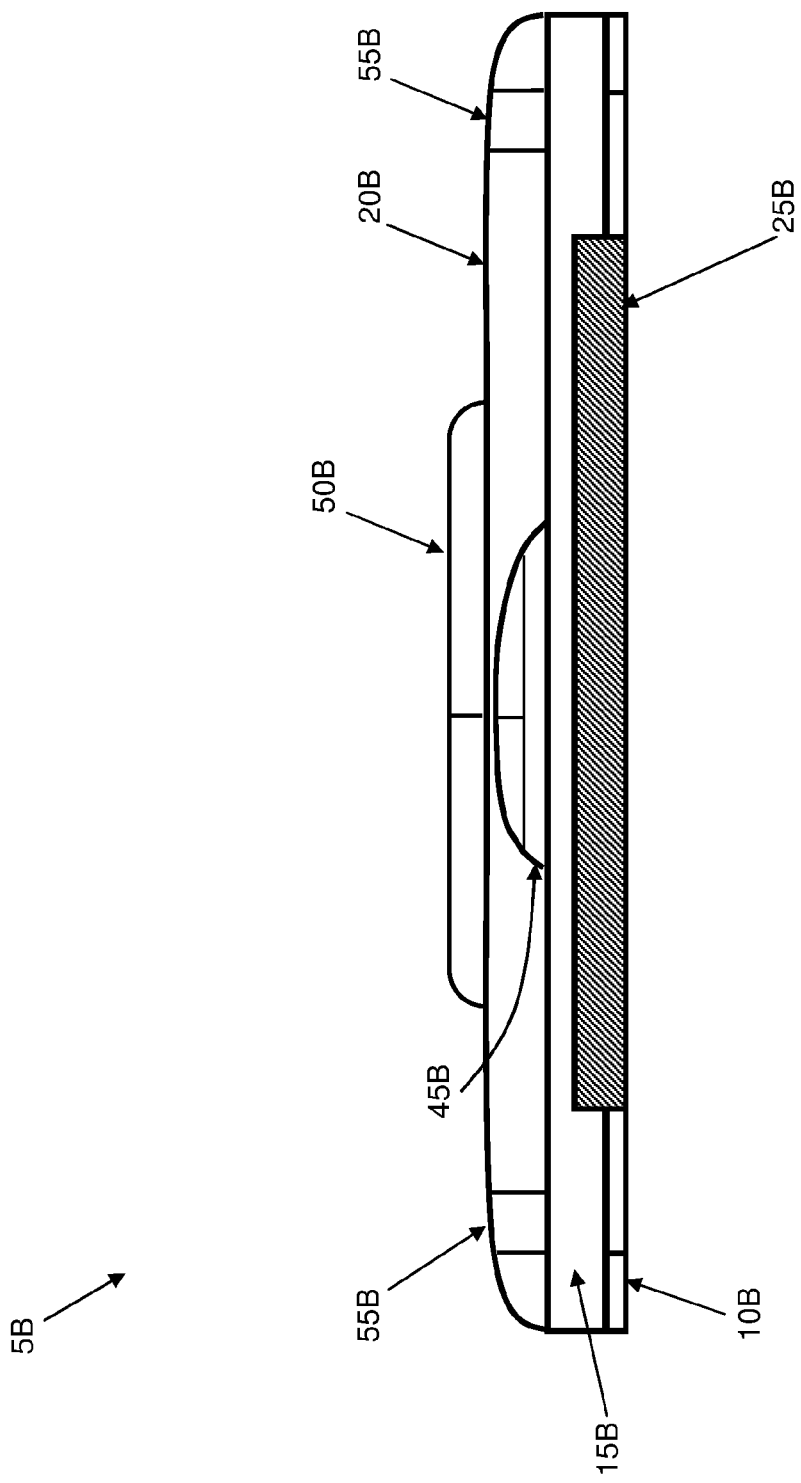

Looking next at FIGS. 13 and 14, there is shown another mechanical vacuum dressing 5B formed in accordance with the present invention. Mechanical vacuum dressing 5B is generally similar to mechanical vacuum dressings 5 and 5A described above, except that the aforementioned pull tabs 50 and 50A are replaced by pull ridges 50B and the aforementioned external one-way valves 55 and 55A are replaced by one or more slit valves 55B.

In use, when pull ridges 50B are pulled upward, external valve layer 20B is tented above internal valve layer 15B, creating suction within the chamber (not shown in FIGS. 13 and 14) which is disposed between the tented external valve layer 20B and the underlying internal valve layer 15B. As this suction is created, adhesive layer 10B flexes and the edges of the wound are drawn together, internal one-way valve 45B opens, air from the wound site is actively drawn into the chamber which is disposed between the tented external valve layer 20B and the underlying internal valve layer 15B, and exudate from the wound is actively drawn into absorbent dressing 25B (FIG. 14). When pull ridges 50B are released, the elastomeric material of external valve layer 20B causes external valve layer 20B to return back to its previous configuration, with air within the chamber (which is disposed between the tented external valve layer 20B and the underlying internal valve layer 15B) being vented out slit valves 55B.

Significantly, by virtue of the airtight seal of adhesive layer 10B against the skin of the patient, internal one-way valve 45B and slit valves 55B, the suction created within the chamber (which is disposed between the tented external valve layer 20B and the underlying internal valve layer 15B) will continue to be applied to the wound even after pull ridges 50B are released, mechanically holding the wound edges together and continuing to draw exudate out of the wound and into absorbent dressing 25B.

Flap Valve Mechanical Vacuum Dressing

Figure 14A:
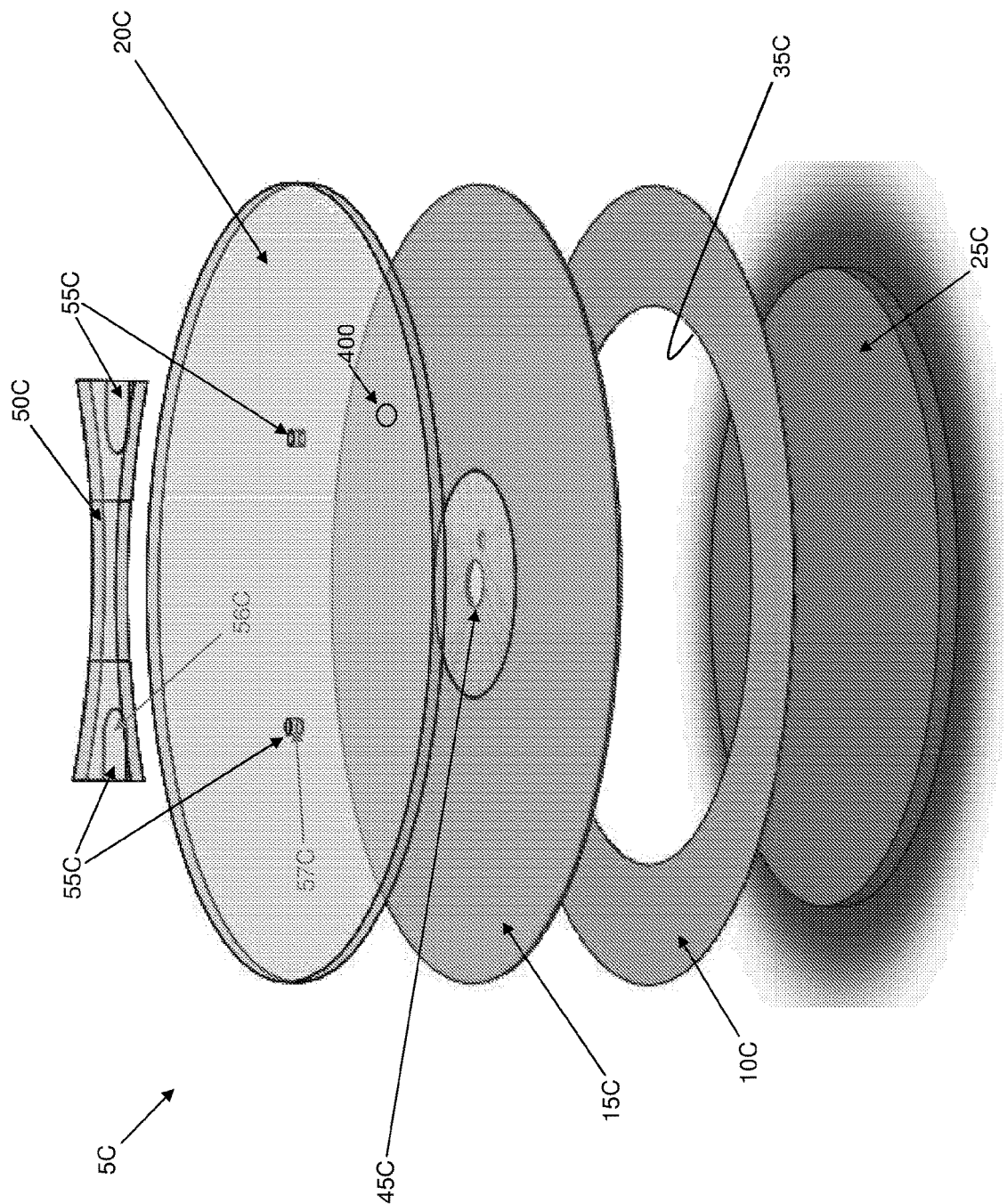
Figure 14C:
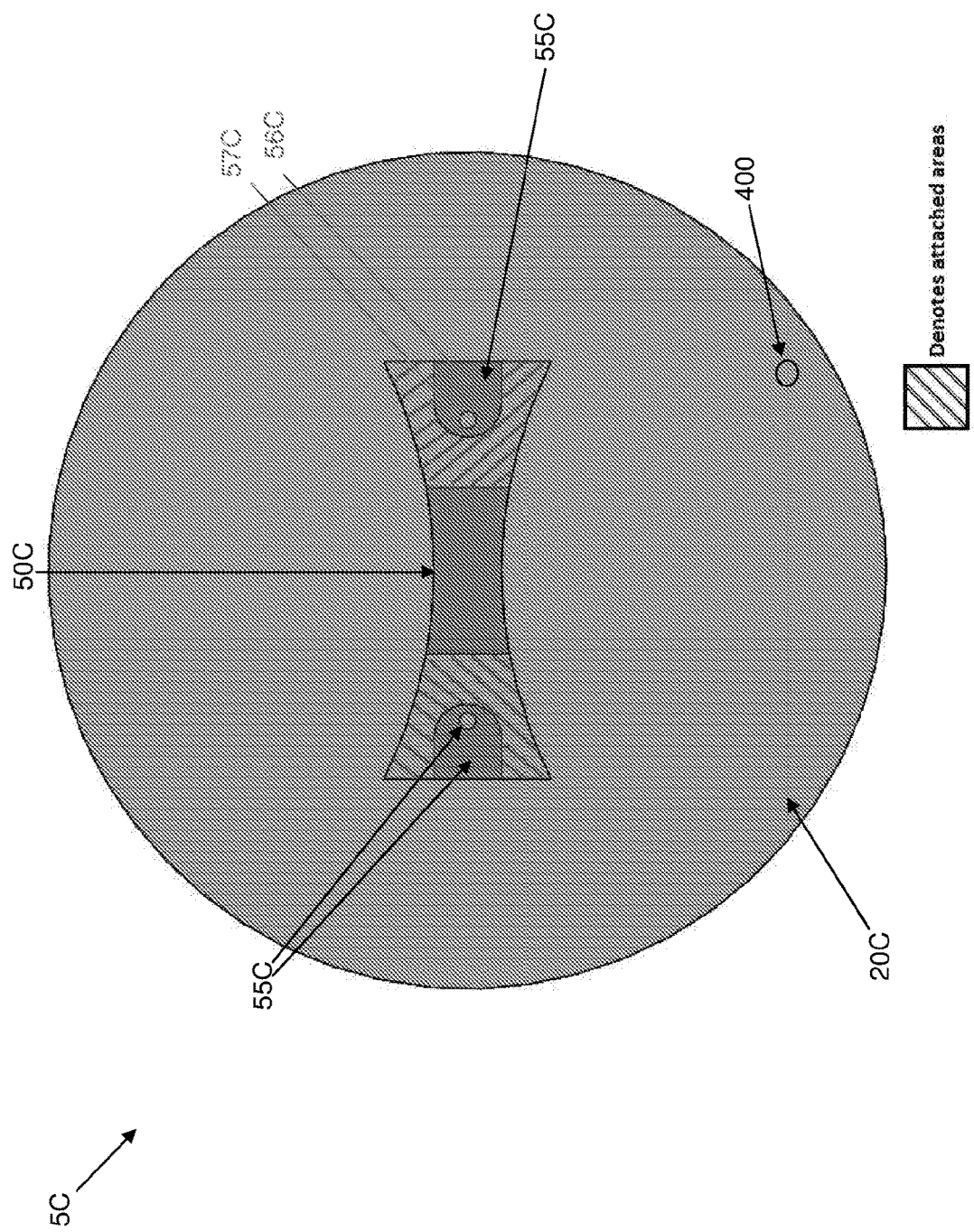

Looking next at FIGS. 14A-14C, there is shown another mechanical vacuum dressing 5C formed in accordance with the present invention. Mechanical vacuum dressing 5C is generally similar to mechanical vacuum dressing 5B, except that pull ridges 50B and slit valves 55B are replaced by a soft pull-handle 50C whose two ends are attached to external valve layer 20C and comprise flap valves 55C meant to allow fluid flow out from between external valve layer 20C and internal valve layer 15C. The ends of soft pull-handle 50C are attached to external valve layer 20C such that the edges are fixed and the center portions are unattached. These unattached center portions create flaps 56C which overlay openings 57C that extend through external valve layer 20C to the space between external valve layer 20C and internal valve layer 15C. Flaps 56C are free to lay flat over openings 57C, stopping passage of fluid therethrough, or flaps 56C are free to flap open, allowing passage of fluid therethrough, depending on actuation of external valve layer 20C. Together, each flap 56C and opening 57C comprises a one-way flap valve 55C.

In use, when soft pull-handle 50C is pulled upward, external valve layer 20C is tented above internal valve layer 15C, creating suction within the chamber (not shown in FIGS. 14A-14C) which is disposed between the tented external valve layer 20C and the underlying internal valve layer 15C. As soft pull-handle 50C is pulled upward, flaps 56C at the ends of soft pull-handle 50C lay flat over openings 57C in external valve layer 20C, preventing fluid passage from outside of absorbent dressing 25C (disposed within central opening 35C) to the chamber which is disposed between the tented external valve layer 20C and the underlying internal valve layer 15C and thus creating suction within the chamber. As this suction is created, adhesive layer 10C flexes and the edges of the wound are drawn together, internal one-way valve 45C disposed on the underlying internal valve layer 15C opens, air from the wound site is actively drawn into the chamber which is disposed between the tented external valve layer 20C and the underlying internal valve layer 15C, and exudate from the wound is actively drawn into absorbent dressing 25C. When soft pull-handle 50C is released, the elastomeric material of external valve layer 20C causes it to return back to its previous configuration, with flaps 56C at the ends of soft pull-handle 50C flapping open, allowing fluid within the chamber (which is disposed between the tented external valve layer 20C and the underlying internal valve layer 15C) to be vented out of openings 57C which extend through external valve layer 20C.

Significantly, by virtue of the airtight seal of adhesive layer 100 against the skin of the patient, internal one-way valve 45C and external one-way valve 55C, the suction created within the chamber disposed between the tented external valve layer 20C and the underlying internal valve layer 15C will continue to be applied to the wound even after soft pull-handle 50C is released, mechanically holding the wound edges together and continuing to draw exudate out of the wound and into absorbent dressing 25C.

Removable Handle Mechanical Vacuum Dressing

Figure 15:
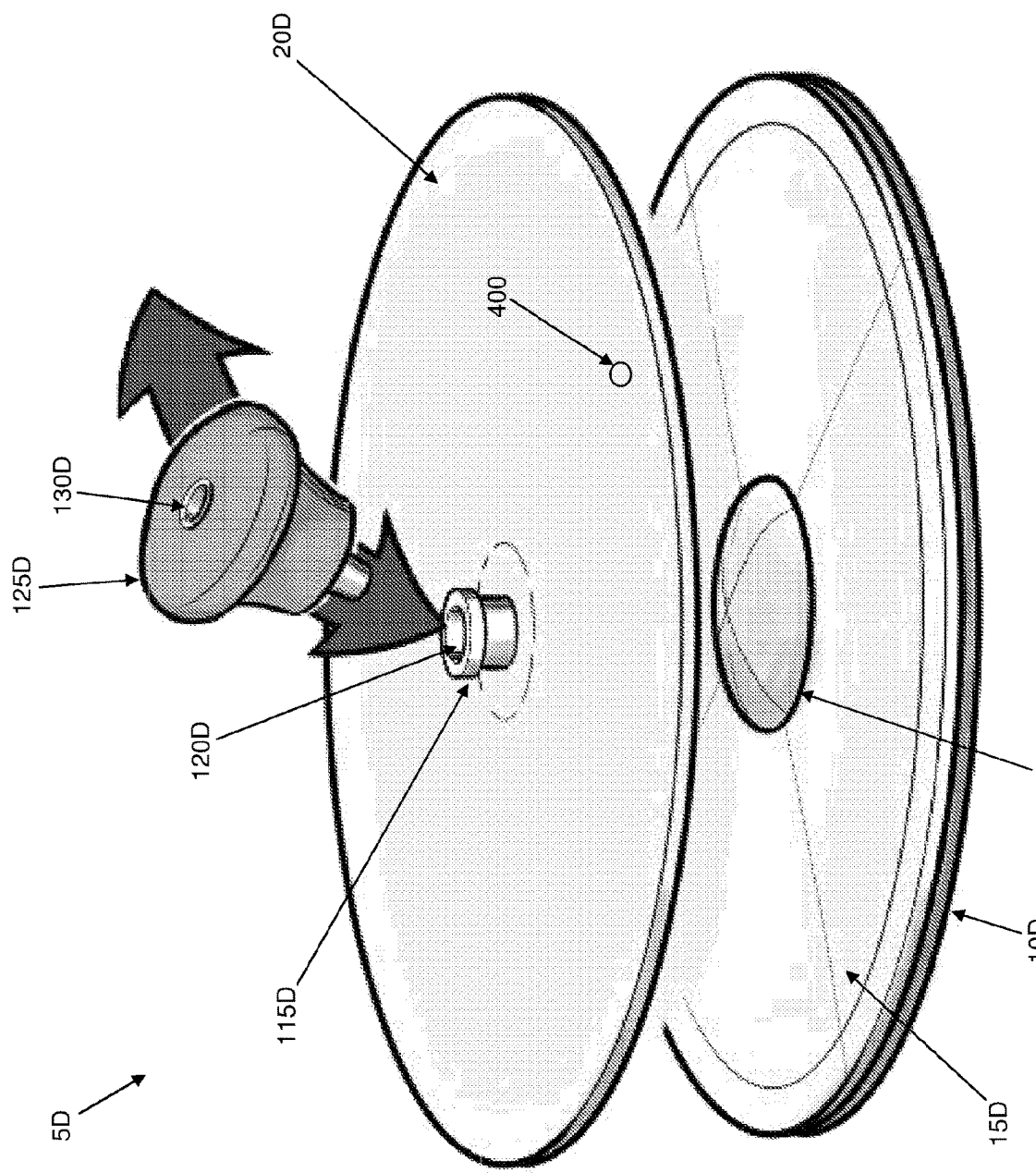
FIG. 15 is a schematic view showing another novel mechanical vacuum dressing formed in accordance with the present invention.

Looking next at FIG. 15, there is shown another mechanical vacuum dressing 5D formed in accordance with the present invention. Mechanical vacuum dressing 5D is generally similar to mechanical vacuum dressings 5, 5A, 5B and 5C described above, except that the aforementioned pull tabs 50, 50A, pull ridges 50B and soft pull-handle 50C, and the aforementioned external one-way valves 55, 55A, slit valves 55B and flap valves 55C, are replaced by a mount 115D having a central opening 120D extending therethrough, with mount 115D having an external one-way valve (not shown in FIG. 15) located within central opening 120D. Mechanical vacuum dressing 5D further comprises a removable handle 125D having a central opening 130D extending therethrough. Removable handle 125D releasably mates with mount 115D when external valve layer 20D is to be tented (i.e., so as to create suction in the chamber (not shown in FIG. 15) disposed between the tented external valve layer 20D and the underlying internal valve layer 15D. Advantageously, removable handle 125D may be removed from mechanical vacuum dressing 5D when tenting of mechanical vacuum dressing 5D is not required, i.e., so as to provide mechanical vacuum dressing 5D with a reduced profile between vacuum pumpings.

In use, when external valve layer 20D is to be tented upwards, removable handle 125D is mounted to mount 115D, and then removable handle 125D is used to tent external valve layer 20D. When external valve layer 20D is tented, suction is created within the chamber (not shown in FIG. 15) which is disposed between the tented external valve layer 20D and the underlying internal valve layer 15D. As this suction is created, adhesive layer 10D flexes and the edges of the wound are drawn together and the internal one-way valve 45D opens, air from the wound site is actively drawn into the chamber which is disposed between the tented external valve layer 20D and the underlying internal valve layer 15D, and exudate from the wound is actively drawn into the absorbent dressing (not shown in FIG. 15) which is disposed beneath internal valve layer 15D. When removable handle 125D is released, the elastomeric material of external valve layer 20D causes it to return back to its previous configuration, with air within the chamber (which is disposed between the tented external valve layer 20D and the underlying internal valve layer 15D) being vented out central opening 120D of mount 115D (and the external one-way valve disposed within central opening 120D of mount 115D) and central opening 130D of removable handle 125D.

Significantly, by virtue of the airtight seal of adhesive layer 10D against the skin of the patient, internal one-way valve 45D and the external one-way valve disposed within central opening 120D of mount 115D, the suction created within the chamber which is disposed between the tented external valve layer 20D and the underlying internal valve layer 15D will continue to be applied to the wound even after removable handle 125D is released, mechanically holding the wound edges together and continuing to draw exudate out of the wound and into the absorbent dressing (not shown in FIG. 15) disposed beneath internal valve layer 15D.

Figure 16:
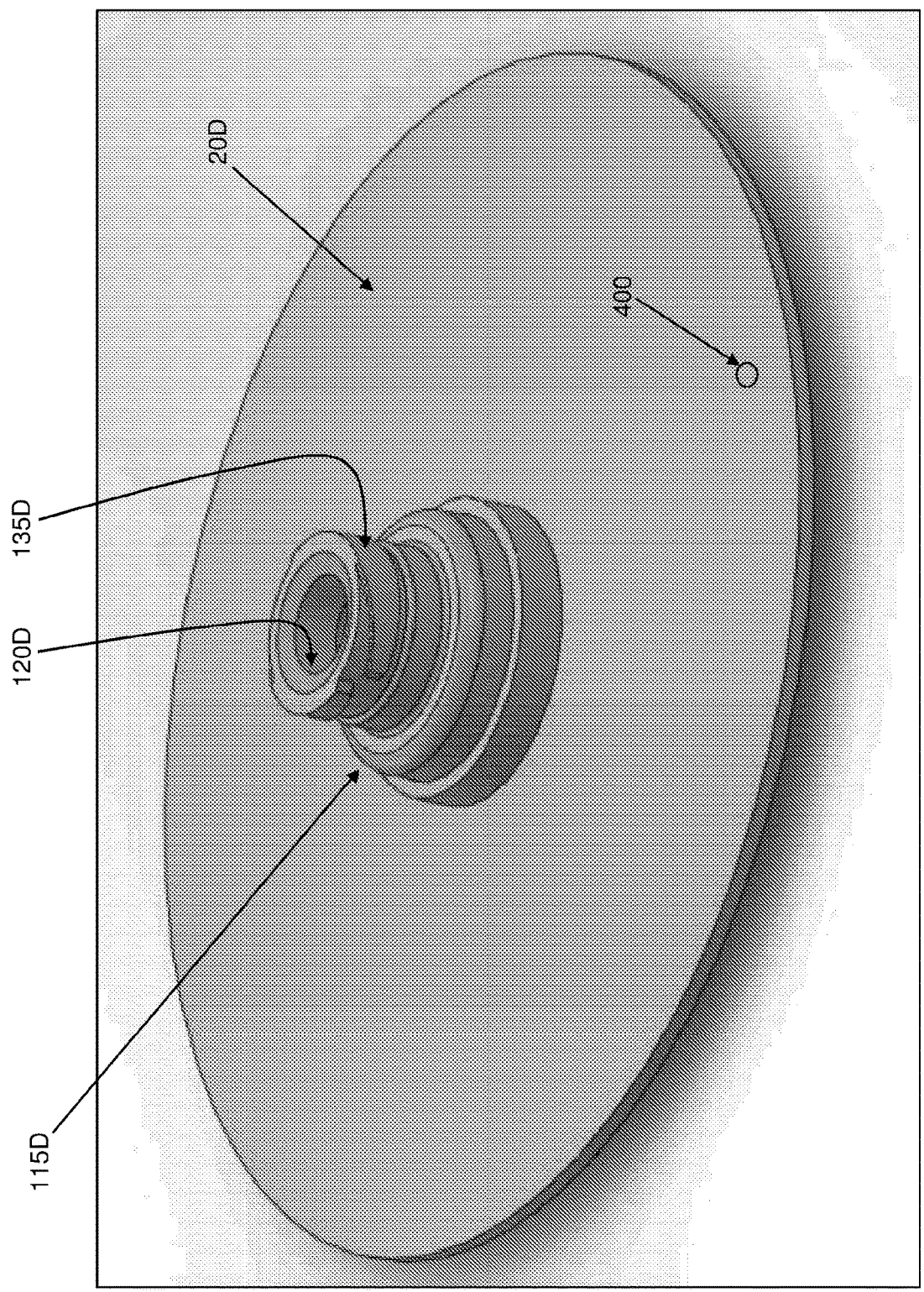
FIG. 16 is a schematic view showing details of a connection mechanism which may be used with the novel mechanical vacuum dressing of FIG. 15.
Figure 19:
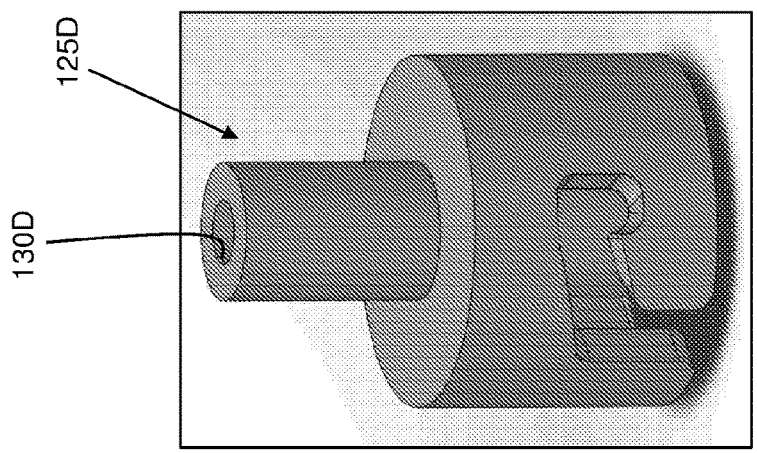
FIGS. 17-20 are schematic views showing alternative connection mechanisms which may be used with the novel mechanical vacuum dressing of FIG. 15.
Figure 18:
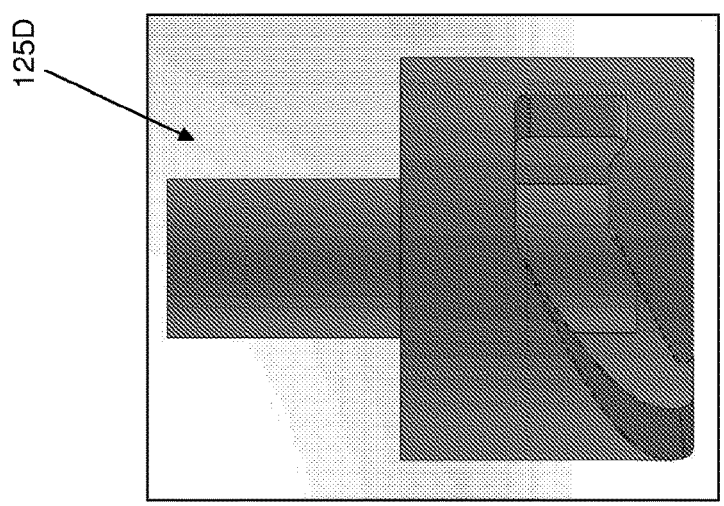
Figure 17:
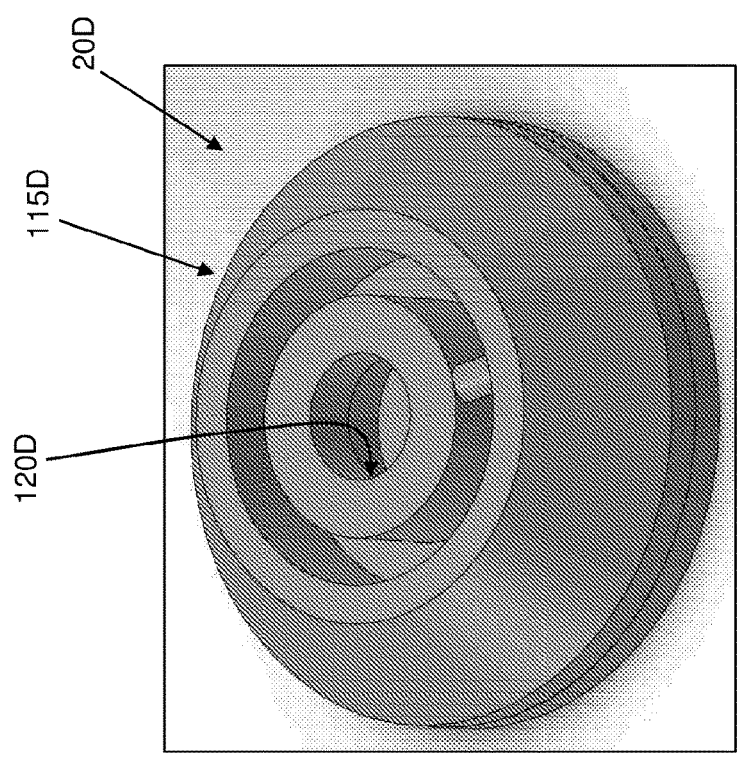
Figure 20:
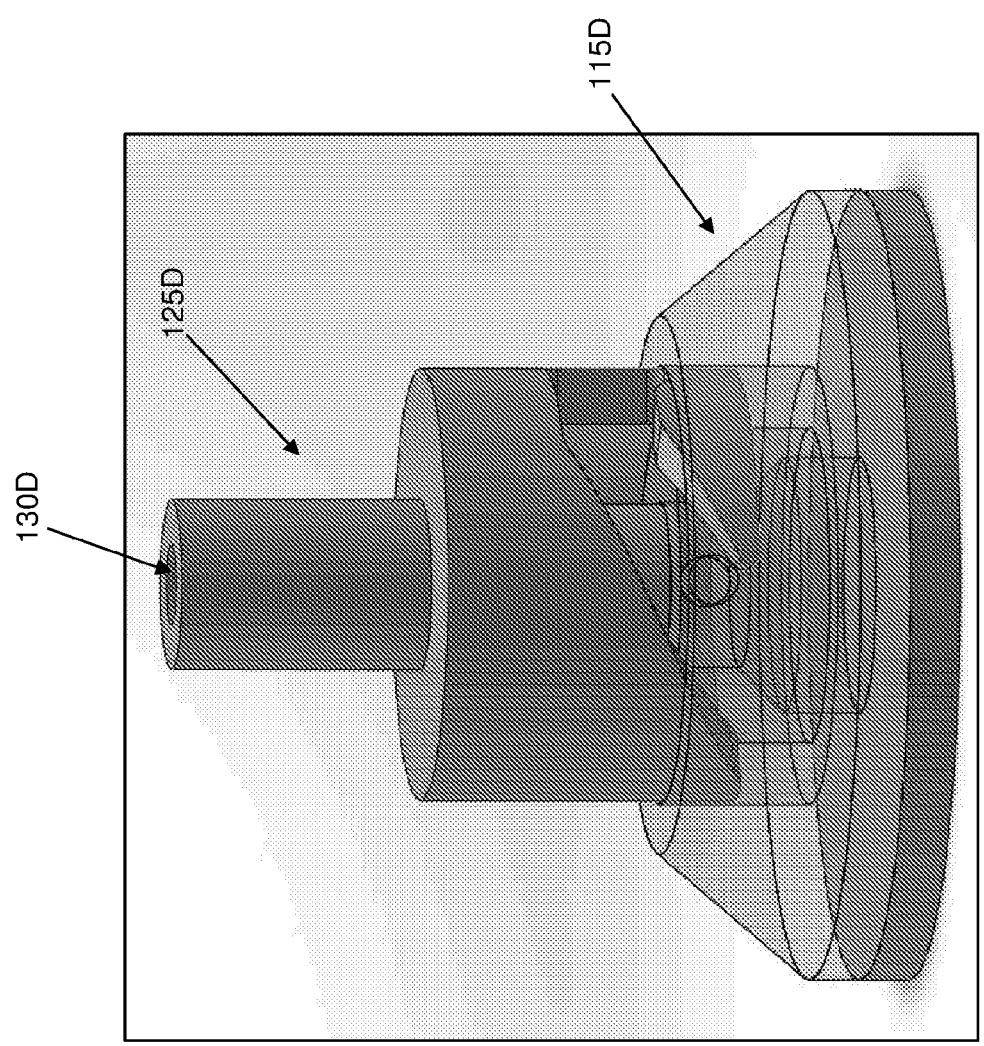

In one preferred form of the invention, and looking now at FIG. 16, mount 115D disposed on external valve layer 20D comprises screw threads 135D, and removable handle 125D (not shown in FIG. 16) comprises counterpart screw threads (not shown in FIG. 16), such that removable handle 125D (not shown in FIG. 16) can be releasably mounted to mount 115D, with central opening 130D (not shown in FIG. 16) in removable handle 125D (not shown in FIG. 16) communicating with central opening 120D in mount 115D.

If desired, alternative mechanisms may be provided for releasably securing removable handle 125D to mount 115D. By way of example but not limitation, FIGS. 17-20 show a "single pin" bayonet mount for releasably mounting removable handle 125D to mount 115D. By way of further example but not limitation, FIGS. 21-25 show a "double pin" bayonet mount for releasably mounting removable handle 125D to mount 115D.

Pinch-Valve Mechanical Vacuum Dressing

Figure 26:
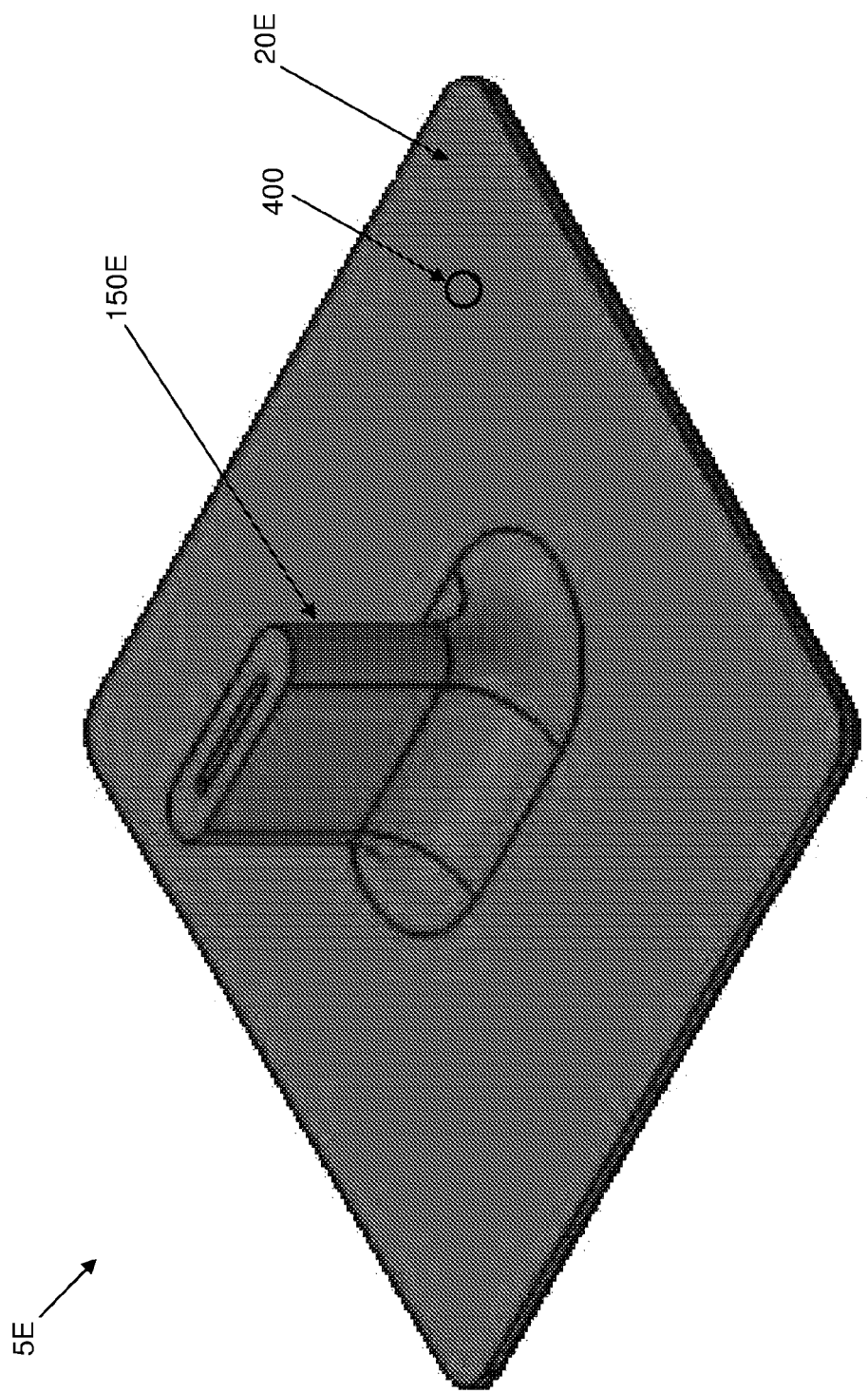
FIGS. 26-28 are schematic views showing another novel mechanical vacuum dressing formed in accordance with the present invention.
Figure 27:
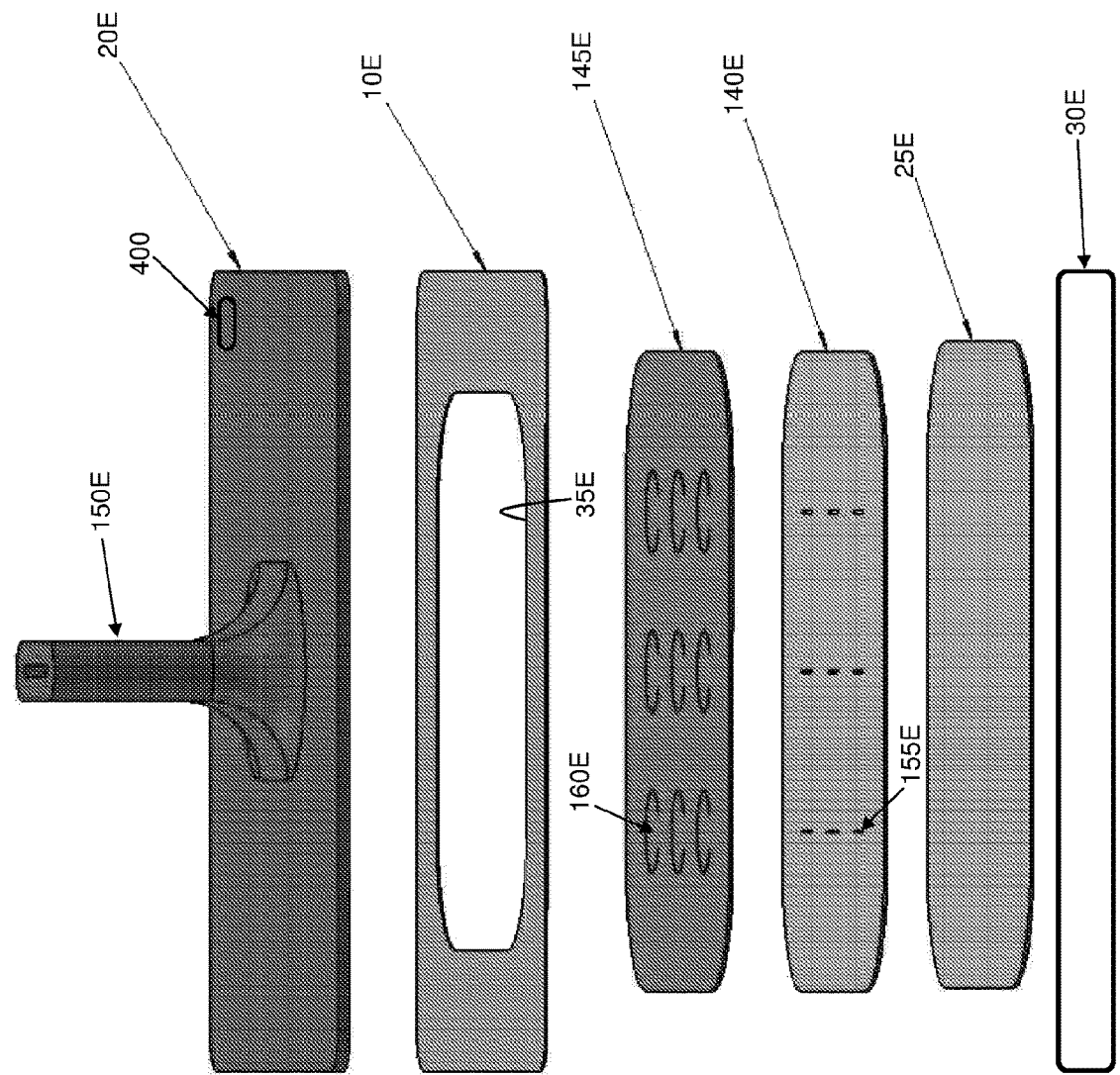
Figure 28:
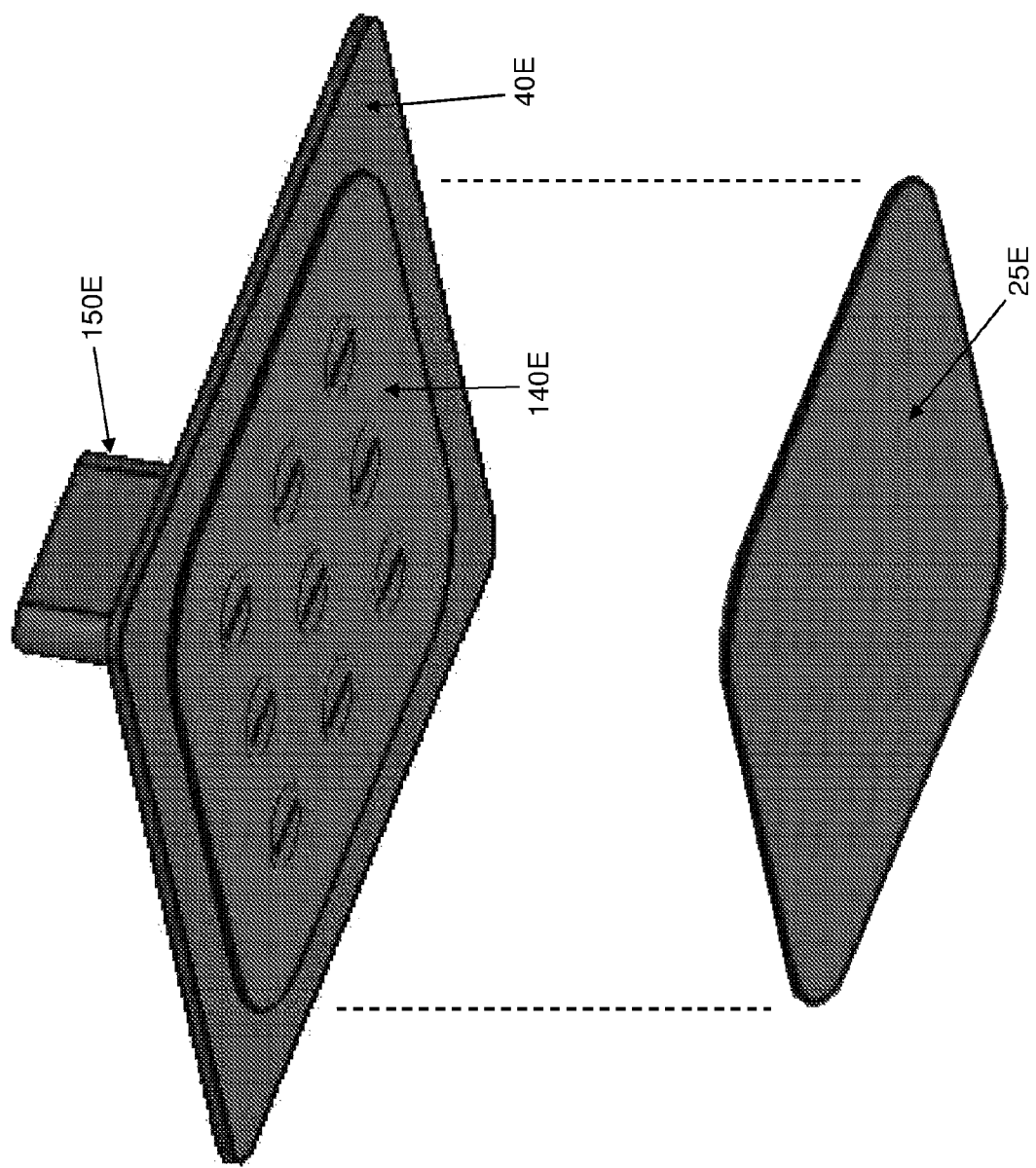

Looking next at FIGS. 26-28, there is shown another novel mechanical vacuum dressing 5E formed in accordance with the present invention. Mechanical vacuum dressing 5E is generally similar to mechanical vacuum dressings 5, 5A, 5B, 5C and 5D described above, except that (i) the aforementioned internal valve layers 15, 15A, 15B, 15C and 15D are replaced by a valve slits layer 140E and a valve flaps layer 145E; and (ii) the aforementioned pull tabs 50, 50A, pull ridges 50B, soft pull-handle 50C and mount 115D/ removable handle 125D, and external one-way valves 55, 55A, slit valves 55B, flap valves 55C and the external one-way valve disposed within the central opening 120D of mount 115D are replaced by a pinch-valve 150E (sometimes referred to as a duckbill valve).

More particularly, as seen in FIG. 27, valve slits layer 140E and valve flaps layer 145E are sandwiched between absorbent dressing 25E and adhesive layer 10E, and external valve layer 20E is disposed against adhesive layer 10E. Release liner 30E is disposed against absorbent dressing 25E and adhesive layer 10E.

Adhesive layer 10E generally comprises a flexible material having a central opening 35E. Adhesive layer 10E is sized so that the perimeter of central opening 35E can circumscribe a wound. Adhesive 40E (FIG. 28) is carried by the bottom surface of adhesive layer 10E. Adhesive layer 10E is constructed so that adhesive layer 10E can form an airtight seal with the skin of a patient. In one preferred form of the invention, absorbent dressing 25E is received within central opening 35E of adhesive layer 10E.

Valve slits layer 140E comprises a flexible material having a plurality of slits 155E. Valve slits layer 140E is sized so as to be substantially the same size as, or larger than, central opening 35E in adhesive layer 10E.

Valve flaps layer 145E comprises a flexible material having a plurality of flaps 160E. Valve flaps layer 145E is sized so as to be substantially the same size as, or larger than, central opening 35E in adhesive layer 10E, and is positioned against the top surface of valve slits layer 140E, with flaps 160E of valve flaps layer 145E overlying slits 155E of valve slits layer 140E.

It will be appreciated that valve slits layer 140E and valve flaps layer 145E effectively create an "inner" valve, or more precisely a plurality of inner valves, which permit(s) fluid to flow from absorbent dressing 25E into the region above valve flaps layer 145E but prevent(s) fluid from flowing back to absorbent dressing 25E. Thus, valve slits layer 140E and valve flaps layer 145E effectively replace the aforementioned internal valve layers 15, 15A, 15B, 15C and 15D, and slits 155E and flaps 160E effectively replace the aforementioned internal one-way valves 45, 45A, 45B, 45C and 45D. This method of forming the inner valve can be advantageous, since it is easy to manufacture, low in cost, low in profile, creates a large number of valve elements which, collectively, function as a large surface area valve to pull an effective suction, etc.

It will also be appreciated that valve slits layer 140E and valve flaps layer 145E may vary in configuration.

Absorbent dressing 25E is preferably formed out of a fluid-permeable, absorptive flexible material, e.g., a woven or non-woven dressing, a foam dressing, etc. In one preferred form of the invention, absorbent dressing 25E is formed out of a hyper-absorptive material, e.g., a hydrophilic foam.

Figure 30:
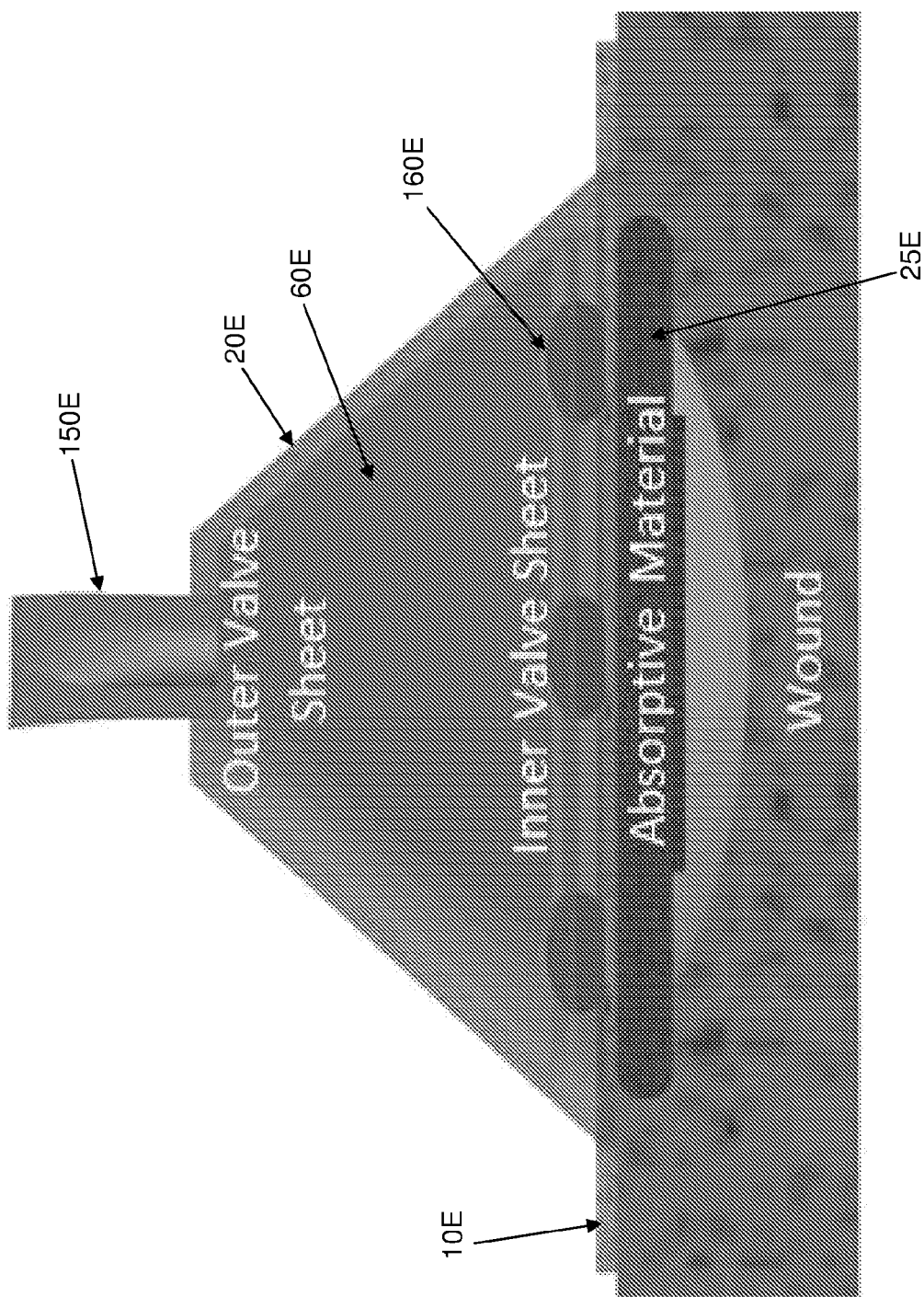

External valve layer 20E generally comprises pinch-valve 150E (sometimes referred to as a duckbill valve). External valve layer 20E is formed out of an elastomeric material such that (i) by pulling upward on pinch-valve 150E, a chamber 60E (FIG. 30) can be created between external valve layer 20E and adhesive layer 10E, whereby to create a negative pressure within chamber 60E, and (ii) when pinch-valve 150E is released, the elastomeric external valve layer 20E will return to its original configuration, whereby to minimize chamber 60E. Pinch-valve 150E is configured to pass fluid from chamber 60E to the region outside mechanical vacuum dressing 5E when pinch-valve 150E is released and elastomeric external valve layer 20E is returning to its original configuration, but to prevent fluid from entering chamber 60E through pinch-valve 150E when elastomeric external valve layer 20E is pulled upward so as to create chamber 60E. In one preferred form of the invention, pinch-valve 150E is configured to pass air from chamber 60E to the region outside mechanical vacuum dressing 5E but to prevent air from entering chamber 60E through pinch-valve 150E.

It will be appreciated that pinch-valve 150E effectively constitutes an "outer" valve which permits fluid (e.g., air) to flow from chamber 60E to the region outside the mechanical vacuum dressing but prevents fluid (e.g., air) from entering chamber 60E through pinch-valve 150E. Thus, pinch-valve 150E effectively replaces the aforementioned external one-way valves 55, 55A, slit valves 55B, flap valves 55C and the external one-way valve disposed within the central opening 120D of mount 115D (and, since pinch-valve 150E is also used to manually tent external valve layer 20E, pinch-valve 150E also effectively replaces the aforementioned pull tabs 50, 50A, pull ridges 50B, soft pull-handle 50C and mount 115D/removable handle 125D).

If desired, a removable frame (not shown) may be provided about the periphery of adhesive layer 10E so as to facilitate maneuvering mechanical vacuum dressing 5E to the wound site and adhering the mechanical vacuum dressing to the skin of the patient. Then, once the mechanical vacuum dressing has been adhered to the skin of the patient, the removable frame (not shown) may be removed, leaving the mechanical vacuum dressing adhered to the skin of the patient. By way of example but not limitation, the removable frame (not shown) may be connected to adhesive layer 10E by a perforation line, a score line, tabs, etc. It should be appreciated that the connection between the removable frame (not shown) and the periphery of adhesive layer 10E is sufficiently robust that mechanical vacuum dressing 5E can be manipulated by means of the removable frame (not shown), but is easily severable upon demand so that the removable frame (not shown) can be separated from mechanical vacuum dressing 5E after mechanical vacuum dressing 5E has been secured to the skin of a patient. Preferably, the removable frame (not shown) does not have an adhesive on its underside, so the removable frame (not shown) comes away easily from the skin of the patient once the mechanical vacuum dressing 5E has been adhered to the skin of the patient.

Figure 29:
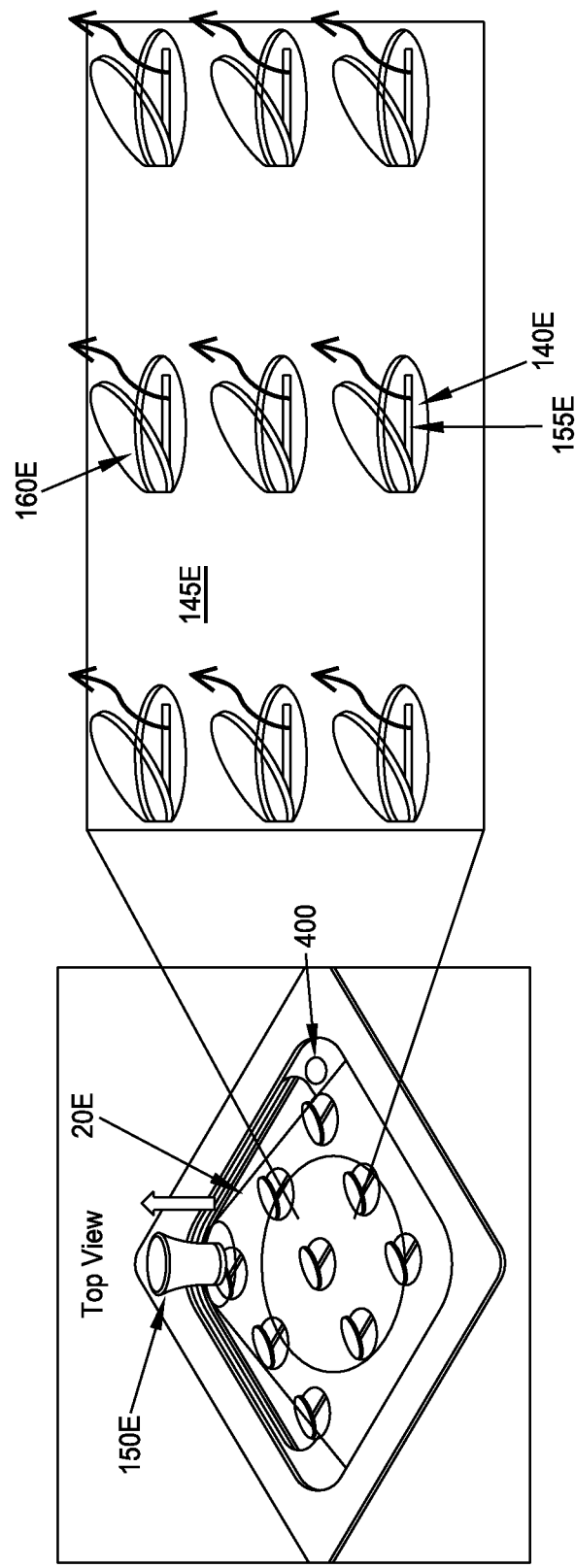
FIGS. 29-31 are schematic views showing operation of the novel mechanical vacuum dressing of FIGS. 26-28.
Figure 31:
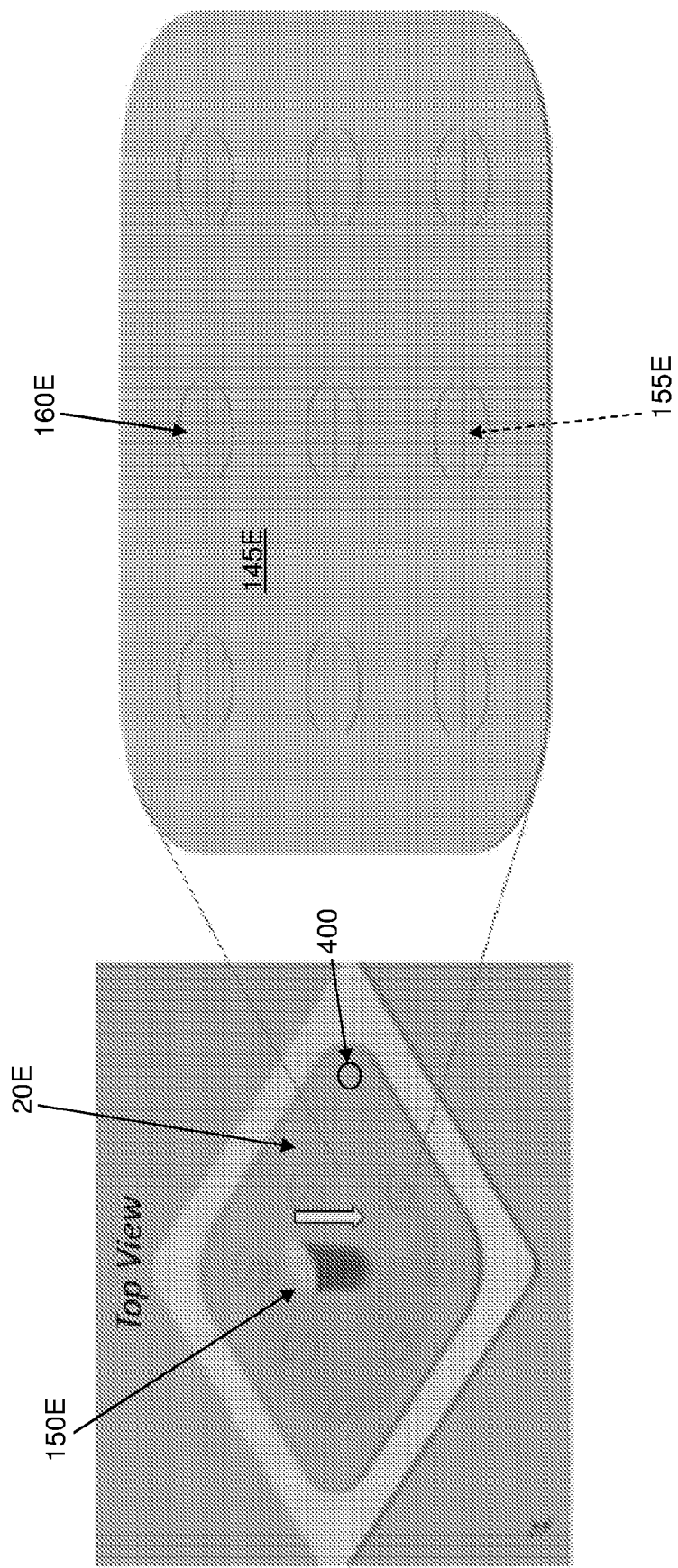

Mechanical vacuum dressing 5E is intended to be used as follows. First, release liner 30E is removed from the bottom surface of adhesive layer 10E. Then mechanical vacuum dressing 5E is positioned against the skin of the patient so that absorbent dressing 25E is positioned against the wound, with adhesive 40E securing mechanical vacuum dressing 5E to the skin of the patient, thereby forming an airtight seal with the skin of the patient, mechanically holding the wound edges together so as to re-establish tissue integrity, and with mechanical vacuum dressing 5E providing a protective healing environment that is occlusive to external air and liquids. Next, pinch-valve 150E is pulled upward, tenting external valve layer 20E (FIGS. 29 and 30) and, by virtue of such tenting, creating suction within chamber 60E. As this suction is created, adhesive layer 10E flexes and the edges of the wound are drawn together, and flaps 160E open, air from the wound site is actively drawn up into chamber 60E, and exudate from the wound is actively drawn into absorbent dressing 25E. Pinch-valve 150E is then released, allowing the elastomeric material of external valve layer 20E to return back to its previous configuration, with fluid within chamber 60E being vented out pinch-valve 150E (see FIG. 31). It should be appreciated that the fluid vented out pinch-valve 150E is substantially all air, with the liquid from the wound being absorbed by absorbent dressing 25E.

Significantly, by virtue of the airtight seal of adhesive layer 10E against the skin of the patient, slits 155E and flaps 160E and pinch-valve 150E, the suction created within chamber 60E will continue to be applied to the wound, mechanically holding the wound edges together and continuing to draw exudate out of the wound and into absorbent dressing 25E.

It will be appreciated that pinch valve 150E may be pulled and released multiple times in order to establish the desired level of suction at the wound site.

Thereafter, whenever it is desired to re-establish negative pressure within chamber 60E (e.g., because of suction leakage), pinch-valve 150E is again grasped, pulled upward and released.

It is anticipated that multiple cycles of pulling suction within chamber 60E may be used, e.g., one cycle after the other to initially establish the desired suction within chamber 60E, or thereafter periodically re-cycling so as to re-establish the desired negative pressure within chamber 60E.

After 1-2 days, mechanical vacuum dressing 5E may be removed from the wound.

Thus it will be seen that mechanical vacuum dressing 5E may be used to mechanically draw the wound edges together so as to re-establish tissue integrity, provide a protective healing environment that is occlusive to external air and liquids, and actively remove exudates from the wound.

Figure 32:
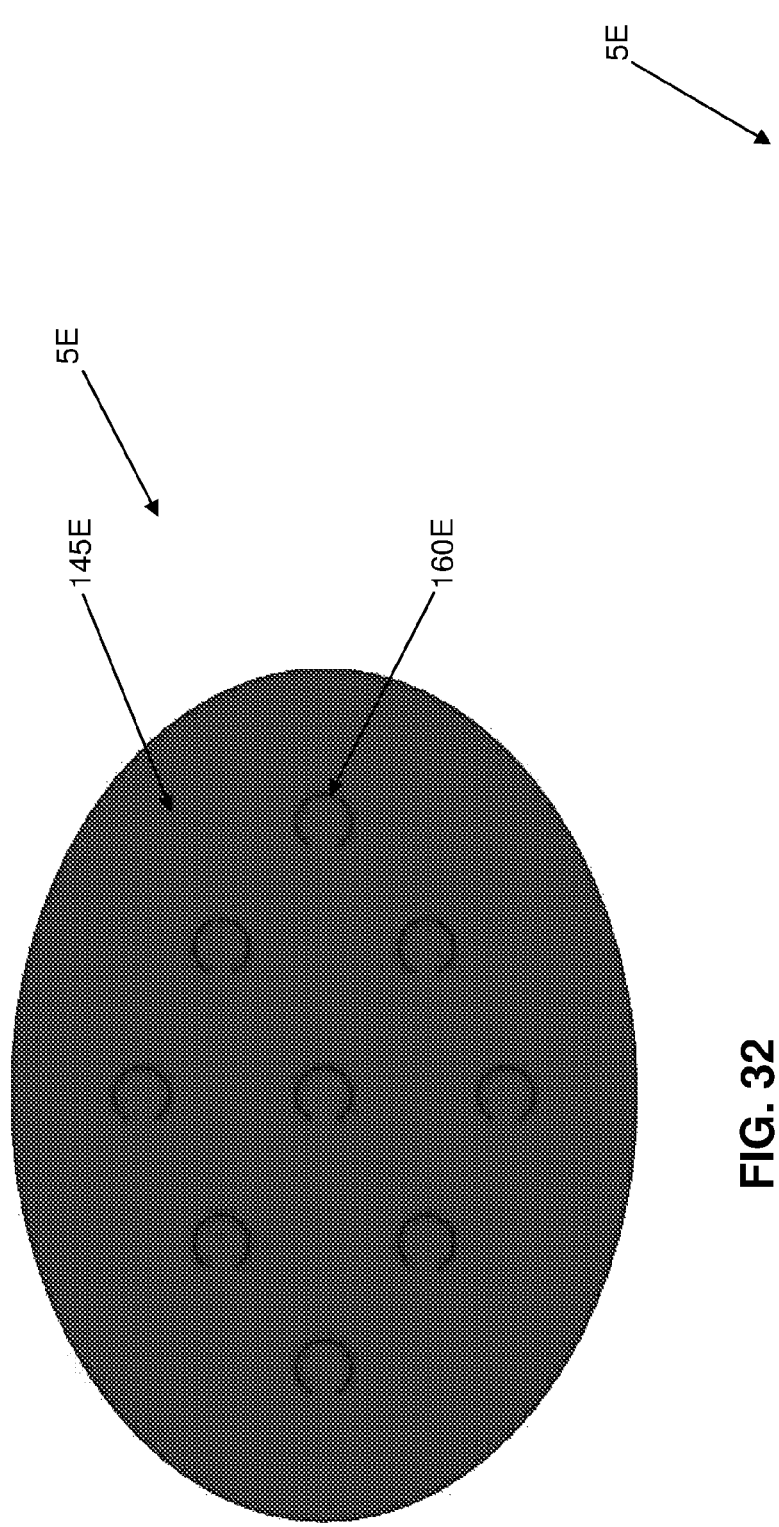
FIGS. 32 and 33 are schematic views showing construction details of still another novel mechanical vacuum dressing formed in accordance with the present invention.
Figure 33:
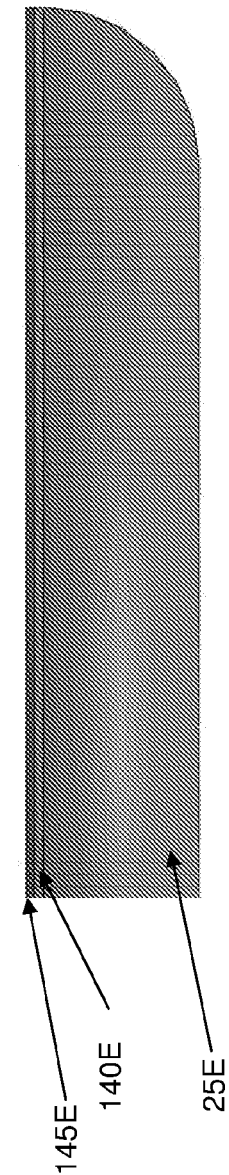

In another preferred form of the invention, and looking now at FIGS. 32 and 33, mechanical vacuum dressing 5E is configured so as to dress longer wounds (e.g., long incisions resulting from a reversed ostomy). Absorbent dressing 25E is configured so as to have a length greater than the absorbent dressing's width, a larger depth, and rounded edges. The increased thickness of the absorbent dressing 25E provides greater compression against the wound and increased exudate retention.

Figure 34:
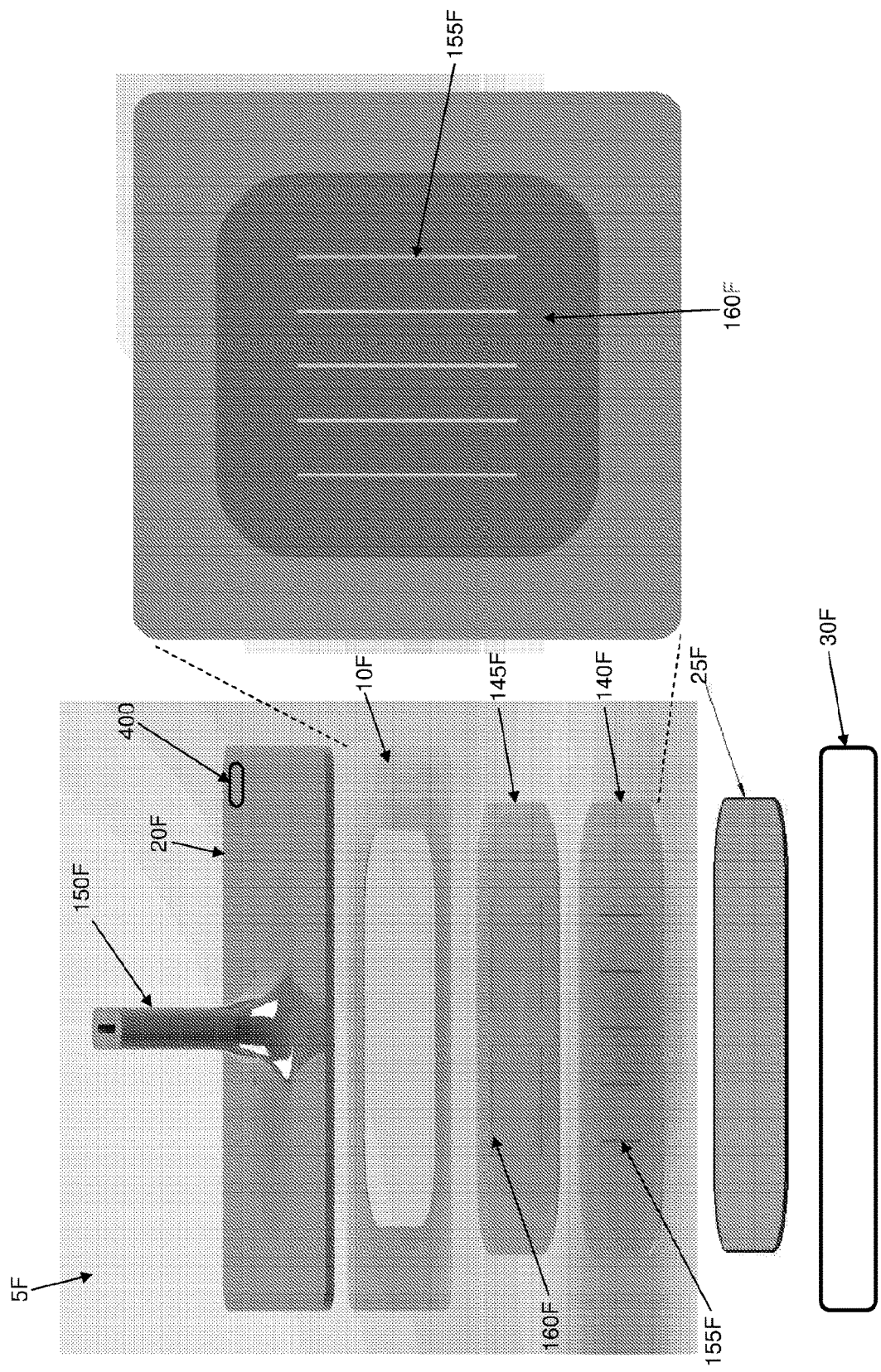
FIG. 34 is a schematic view showing yet another novel mechanical vacuum dressing formed in accordance with the present invention.

Looking next at FIG. 34, there is shown another mechanical vacuum dressing 5F formed in accordance with the present invention. Mechanical vacuum dressing 5F is substantially the same as the aforementioned mechanical vacuum dressing 5E except that, in this form of the invention, the aforementioned valve slits layer 140E and valve flaps layer 145E have the construction shown in FIG. 34. More particularly, in this form of the invention, valve slits layer 140F comprises slits 155F and valve flaps layer 145F comprises narrow openings 160F, with slits 155F and narrow openings 160F being offset from one another when seen in top plan view.

Note that mechanical dressing 5F also comprises adhesive layer 10F, absorbent dressing 25F and release line 30F.

In use, when pinch-valve 150F is pulled upward, tenting external valve layer 20F and creating suction within the interior of mechanical vacuum dressing 5F, valve flaps layer 145F tents slightly, allowing air to pass through slits 155F in valve slits layer 140F, enter the space between valve slits layer 140F and valve flaps layer 145F, pass through the narrow openings 160F in valve flaps layer 145F, and then enter the tented interior of mechanical vacuum dressing 5F. Thereafter, when pinch-valve 150F is released, so that the elastomeric external valve layer 20F returns to its original configuration, the space between valve slits layer 140F and valve flaps layer 145F closes so as to seal off the wound as pinch-valve 150F vents chamber 60F (not shown in FIG. 34).

Mechanical Vacuum Dressing with a Peristaltic Pump Mechanism

Figure 35:
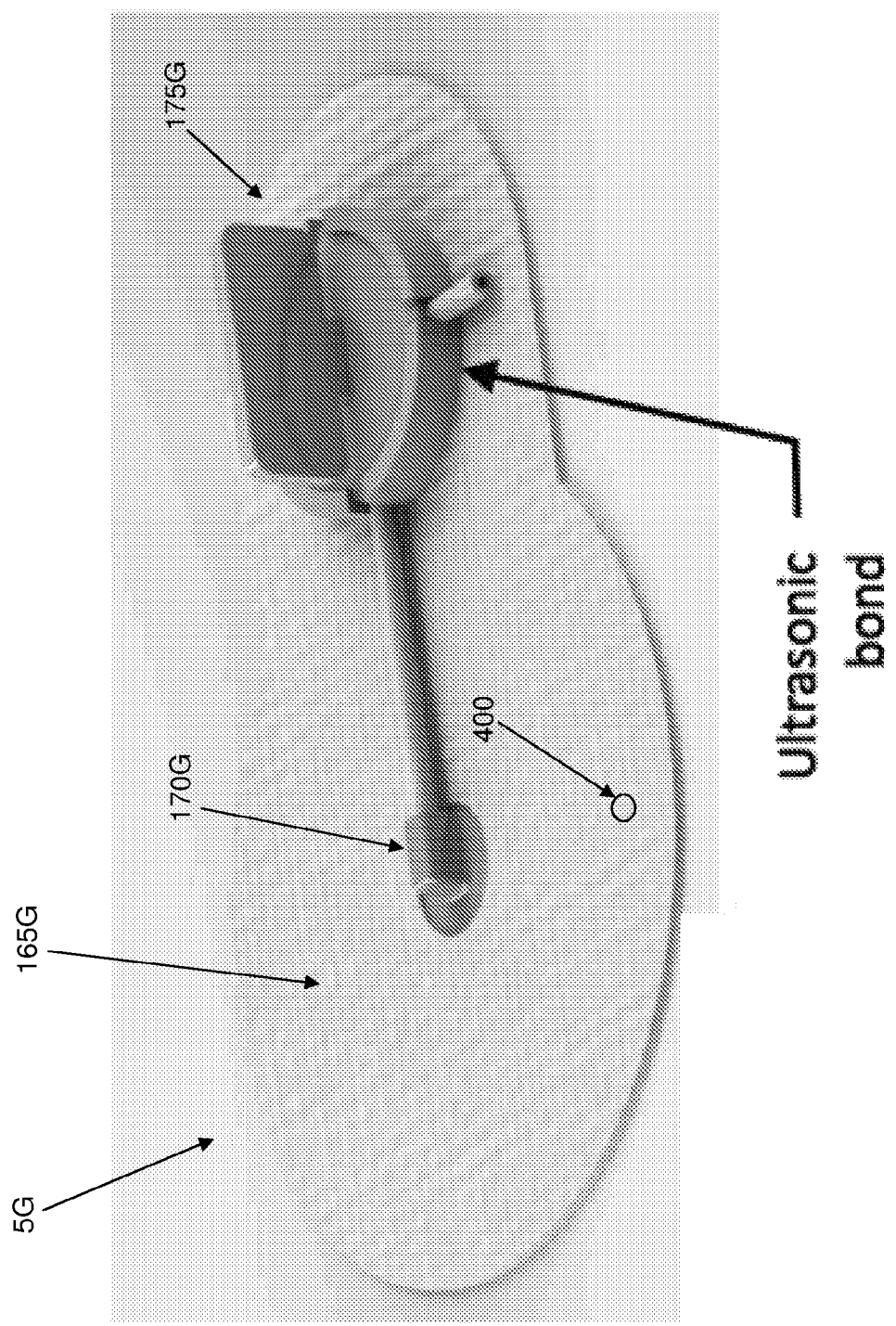
FIGS. 35 and 36 are schematic views showing another novel mechanical vacuum dressing formed in accordance with the present invention, wherein the mechanical vacuum dressing includes a peristaltic pump mechanism.
Figure 36:
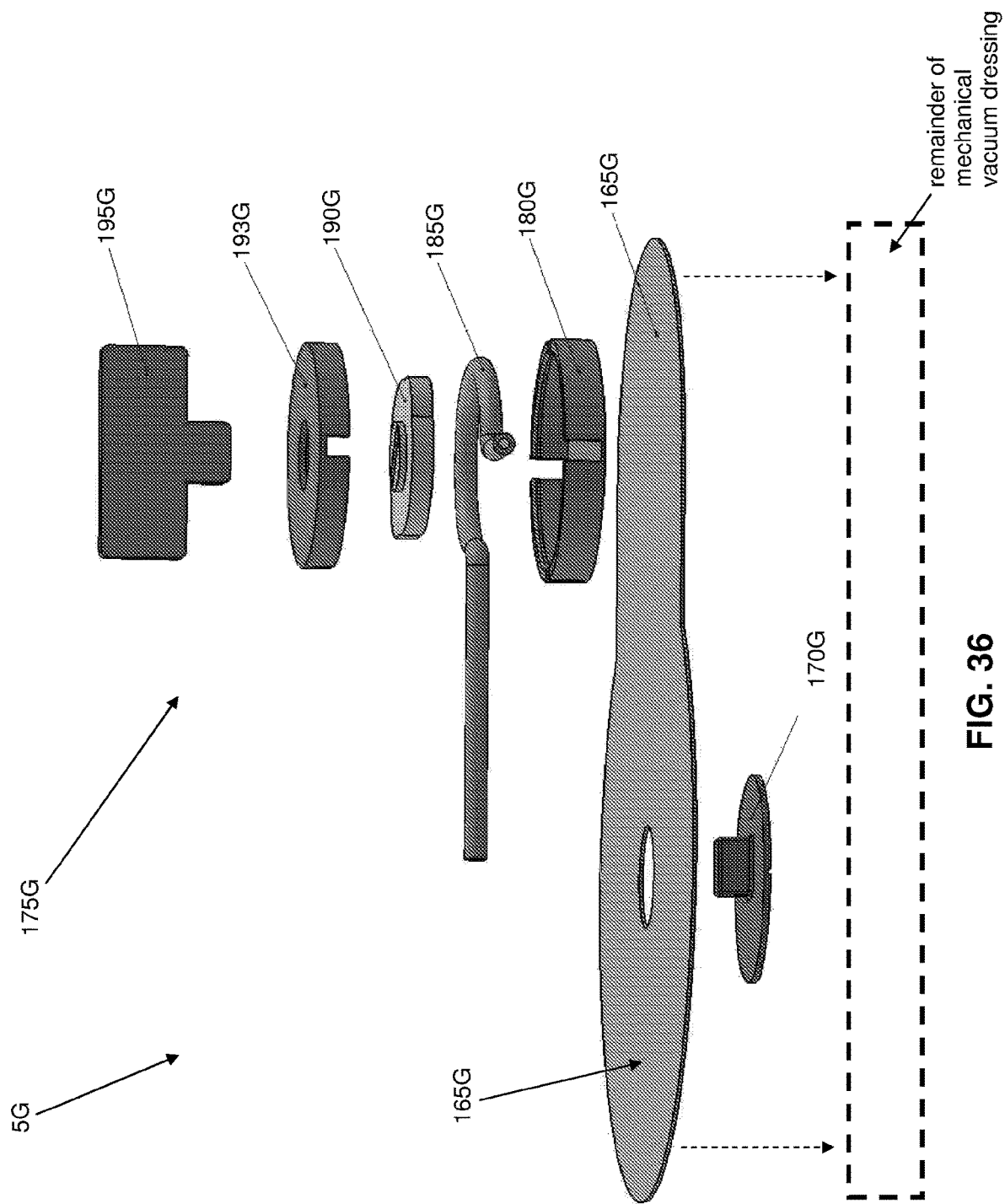

Looking next at FIGS. 35 and 36, there is shown another mechanical vacuum dressing 5G. Mechanical vacuum dressing 5G is generally similar to mechanical vacuum dressing 5 described above, except that the aforementioned external valve layer 20 (and its pull tab 50 and external one-way valve 55) is replaced by a cover layer 165G which is adhered to the remainder of the mechanical vacuum dressing. Cover layer 165G comprises a flange elbow connector 170G and a peristaltic pump mechanism 175G. Peristaltic pump mechanism 175G may be of the sort well known in the art, e.g., such as the peristaltic pump mechanism shown in FIGS. 35 and 36, and comprising a pump outer housing 180G, a tube 185G, a pump roller 190G, a pump inner housing 193G and a crank key 195G, with tube 185G being connectable to flange elbow connector 170G (which is itself secured to cover layer 165G). In one form of the invention, peristaltic pump mechanism 175G may be permanently secured to cover layer 165G. In another form of the invention, tube 185G of peristaltic pump mechanism 175G may be connectable to flange elbow connector 170G at the time of use. A one-way check valve (not shown) may be added to the output of tube 185G so as to ensure that no air from the surrounding environment is able to leak through peristaltic pump mechanism 175G and cause a loss of negative pressure.

In use, when suction is to be drawn within the absorbent dressing disposed beneath cover layer 165G and flange elbow connector 170G, peristaltic pump mechanism 175G is used to apply suction to flange elbow connector 170G, whereby to create suction within the absorbent dressing (not shown in FIGS. 35 and 36). As this suction is created, the adhesive layer (not shown in FIGS. 35 and 36) of mechanical vacuum dressing 5G flexes and the edges of the wound are drawn together and exudate from the wound is actively drawn into the absorbent dressing (not shown in FIGS. 35 and 36).

Figure 38:
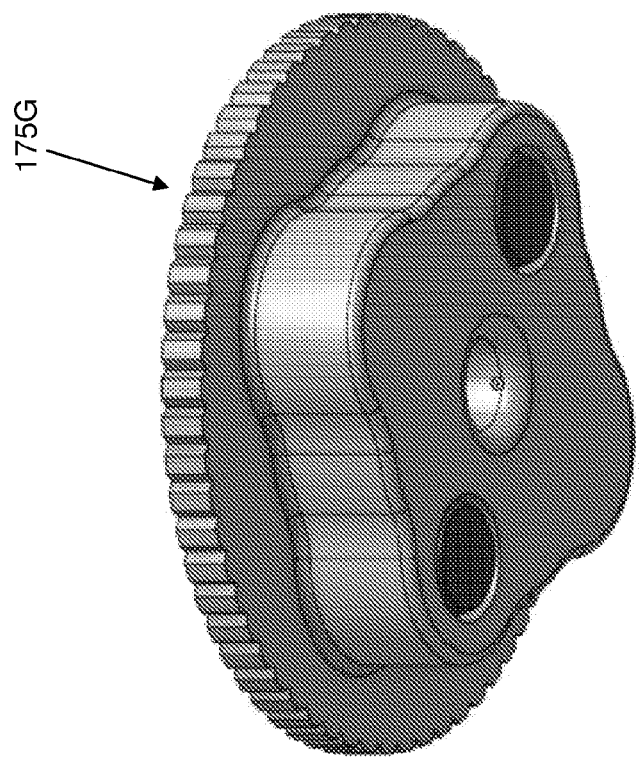
FIGS. 37 and 38 are schematic views showing other peristaltic pump mechanisms which may be used with the novel mechanical vacuum dressing of FIGS. 35 and 36.
Figure 37:
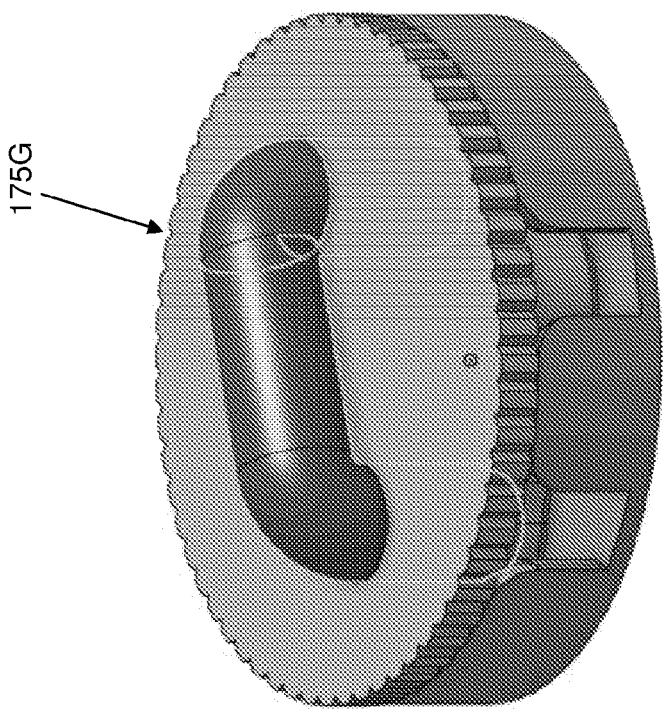
Figure 39:
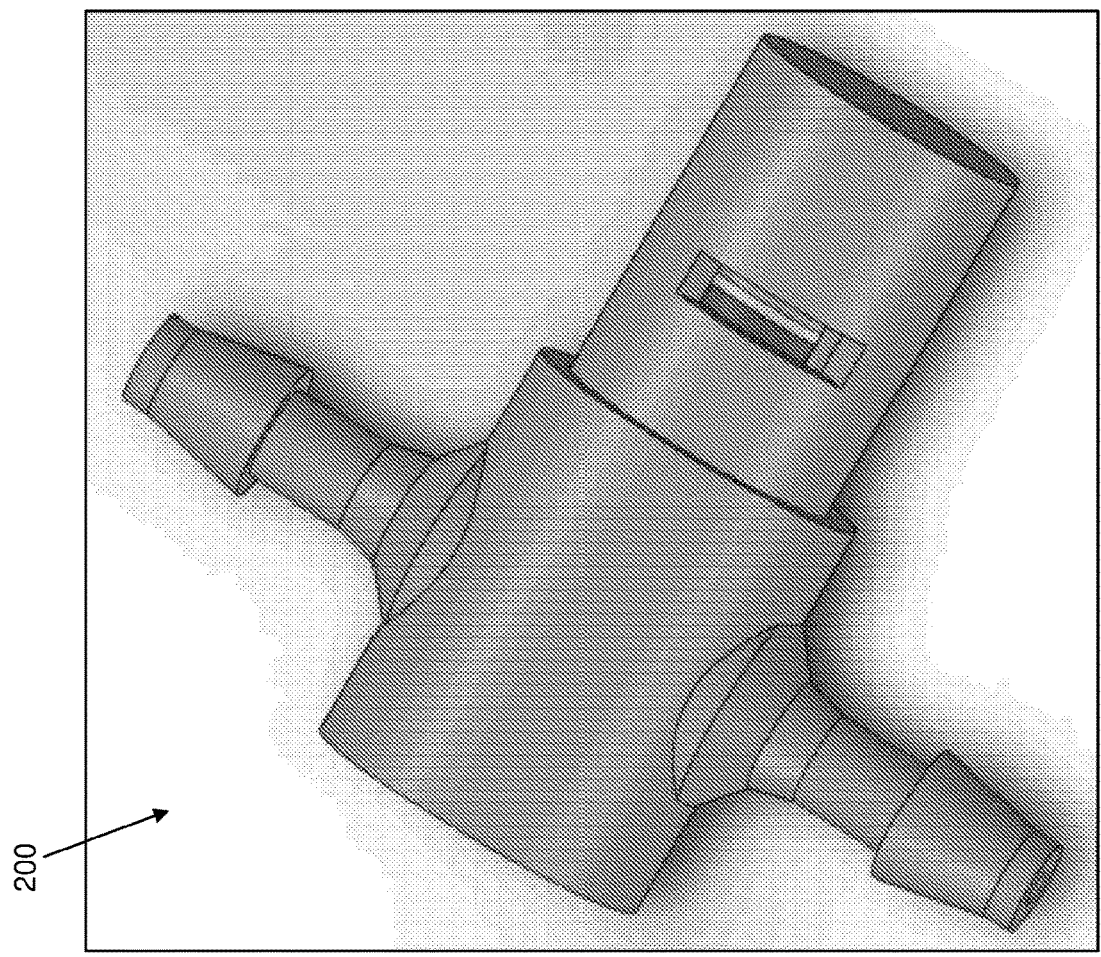
FIGS. 39, 40A, 40B and 40C are schematic views showing a pressure gauge which may be used with the novel mechanical vacuum dressings of the present invention.
Figure 40B:
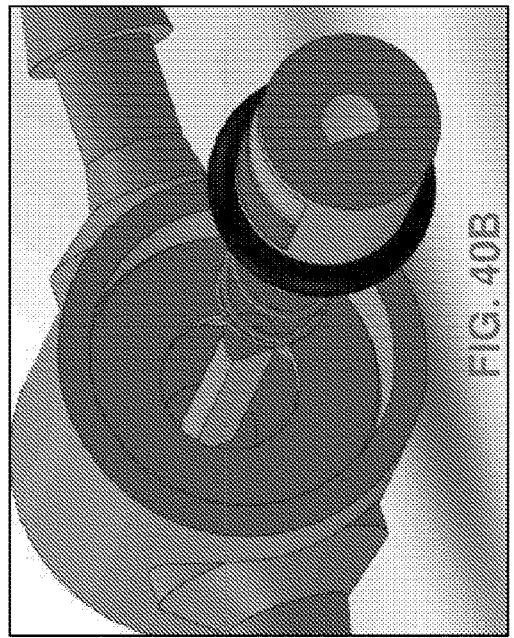
Figure 40A:
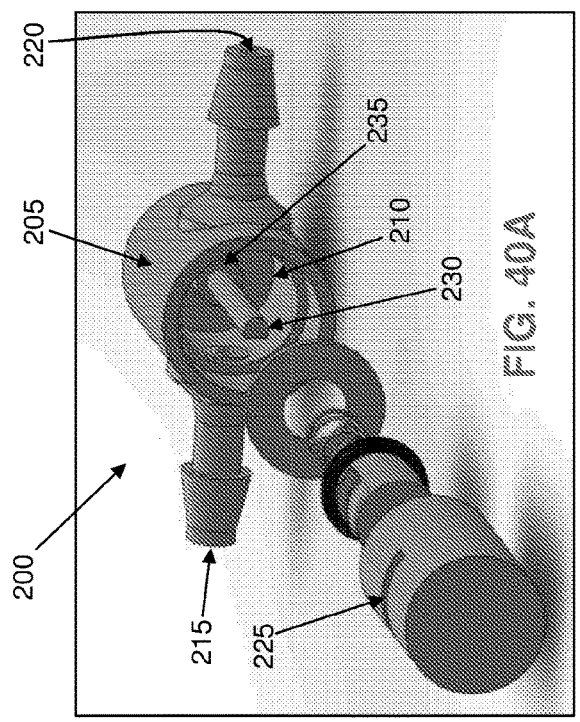
Figure 40C:
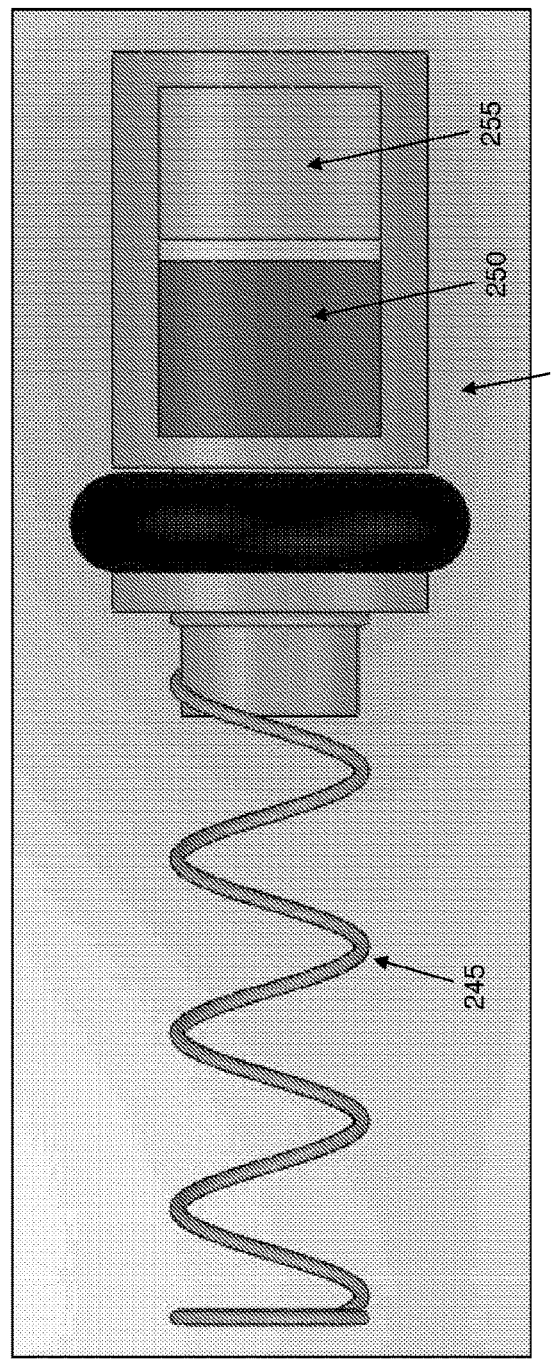

An alternative form of peristaltic pump mechanism 175G is shown in FIGS. 37 and 38.

Pressure Gauge

If desired, a pressure gauge may be provided to give medical personnel a visual indication of insufficient/sufficient suction within the mechanical vacuum dressing. By way of example but not limitation, a pressure gauge 200 is shown in FIGS. 39 and 40A, 40B and 40C. Pressure gauge 200 generally comprises a housing 205 having a chamber 210, a first port 215, a second port 220, and a window 225. A post 230 having a stop shoulder 235 is disposed within chamber 210. A color-coded piston 240 is movably mounted on post 230, with a spring 245 biasing color-coded piston 240 away from stop shoulder 235 so that a red indicator 250 is normally displayed in window 225 when no suction is applied to pressure gauge 200. When pressure gauge 200 is connected in an air line, with port 215 being connected to a chamber within which an appropriate level of negative pressure is to be established and port 220 is connected to a suction source, and when adequate suction is thereafter pulled at port 220, color-coded piston 240 will be pulled against the power of spring 245 towards stop shoulder 235 so that green indicator 255 is displayed in window 225, thereby showing that the appropriate level of negative pressure has been established in the chamber to which 215 is connected.

Pressure gauge 200 may be used with the aforementioned mechanical vacuum dressings 5, 5A, 5B, 5C, 5D, 5E, 5F and 5G, so as to provide a visual indication of insufficient/sufficient pressure within the mechanical vacuum dressings. Where pressure gauge 200 is used with mechanical vacuum dressings 5, 5A, 5B, 5C, 5D, 5E, 5F or 5G, one port of pressure gauge 200 is connected to the mechanical vacuum dressing, e.g., via a fitting 400, and the second port is sealed.

"Finger Press" Mechanical Vacuum Dressing

Looking next at FIGS. 41A-41E, there is shown another mechanical vacuum dressing 300 formed in accordance with the present invention. Mechanical vacuum dressing 300 generally comprises a bottom layer 305 and a top layer 310.

Bottom layer 305 is preferably a substantially flat planar sheet comprising a flexible material having an opening 315. Bottom layer 305 preferably comprises adhesive 320 which extends over the portion of bottom layer 305 which contacts the skin of a patient. Bottom layer 305 preferably also comprises fold-over tabs 325. Adhesive 320 does not extend over fold-over tabs 325. Fold-over tabs 325 can be used to help maintain the negative pressure of the mechanical vacuum dressing once negative pressure has been established within the mechanical vacuum dressing (see below). Absorptive material layer 330 is disposed in opening 315 of bottom layer 305. A release liner 332 is preferably disposed across the bottom of bottom layer 305.

Top layer 310 generally comprises a planar sheet affixed to bottom layer 305. Top layer 310 is affixed to bottom layer 305 so as to define a first passageway 335, a chamber 340 and one or more second passageways 345.

First passageway 335 is rendered permanently "open" by virtue of the fact that an arcuate support member 350 separates top layer 310 from bottom layer 305.

Chamber 340 is characterized by an upwardly extending dome 342 which is preferably filled with an open-cell foam 343.

At the second passageways 345, bonding between top layer 310 and bottom layer 315 is intentionally prevented. Second passageways 345 act as something of flap valves, in the sense that fluid at positive pressure within the opening 315, first passageway 335, and chamber 340 causes the top layer 310 to separate slightly from the bottom layer 305 at second passageways 345, whereby fluid can pass through the second passageways 345 and be expelled into the surrounding environment. Fluid at negative pressure within the opening 315, first passageway 335 and chamber 340 causes top layer 310 to be pulled down against bottom layer 305 at second passageways 345, whereby an air-tight seal is formed and air is prevented from entering the mechanical vacuum dressing 300 through second passageways 345. Fold-over tabs 325 may be used to selectively seal the second passageways 345 (where the passageways meet the edge of the mechanical vacuum dressing) after a vacuum has been established in opening 315 so as to ensure a leak-free seal over an extended period of time. By way of example but not limitation, fold-over tabs 325 can be used to help maintain the negative pressure of the mechanical vacuum dressing once negative pressure has been established within opening 315 of the mechanical vacuum dressing.

If desired, a removable frame (not shown) may be provided about the periphery of bottom layer 305 so as to facilitate maneuvering mechanical vacuum dressing 300 to the wound site and adhering the mechanical vacuum dressing to the skin of the patient. Then, once the mechanical vacuum dressing has been adhered to the skin of the patient, the removable frame (not shown) may be removed, leaving the mechanical vacuum dressing adhered to the skin of the patient. By way of example but not limitation, the removable frame (not shown) may be connected to bottom layer 305 by a perforation line, a score line, tabs, etc. It should be appreciated that the connection between the removable frame (not shown) and the periphery of bottom layer 305 is sufficiently robust that mechanical vacuum dressing 300 can be manipulated by means of the removable frame (not shown), but is easily severable upon demand so that the removable frame (not shown) can be separated from mechanical vacuum dressing 300 after the mechanical vacuum dressing 300 has been secured to the skin of a patient. Preferably, the removable frame (not shown) does not have an adhesive on its underside, so the removable frame (not shown) comes away easily from the skin of the patient once the mechanical vacuum dressing 300 has been adhered to the skin of the patient.

In use, release liner 332 is removed from bottom layer 305. Then mechanical vacuum dressing 300 is positioned against the skin of the patient so that absorptive material layer 330 is positioned against the wound, with adhesive 320 securing mechanical vacuum dressing 300 to the skin of the patient, mechanically holding the wound edges together so as to re-establish tissue integrity, whereby mechanical vacuum dressing 300 provides a protective healing environment that is occlusive to external air and liquids. Next, medical personnel use a finger (or tool) to press against top layer 310 immediately above chamber 340 so as to compress dome 342 of chamber 340 and expel air and exudate from opening 315 and absorptive material layer 330. The air passes through first passageway 335 and, since first passageway 335 is at positive pressure, through second passageways 345. When pressure on opening 315 and absorptive material layer 330 is relaxed, second passageways 345 close so as to maintain suction on the wound. The absorptive material layer 330 expands toward its original volume by an amount dependent on its resilience. The negative pressure achieved depends on the volume of fluid expelled when dome 342 of chamber 340 is pressed on by medical personnel and by the volume of chamber 340 after the downward force applied by medical personnel is removed. The negative pressure achieved can, therefore, be controlled by the pressure applied by medical personnel. Furthermore, increasing the resilience of dome 342 of chamber 340 (e.g., by the presence of open-cell foam 343 within chamber 340 or by increasing the resilience of the material used to form dome 342 of chamber 340) will increase the achievable negative pressure. Fold-over tabs 325 may then be folded-over mechanical vacuum dressing 300 so as to seal the mechanical vacuum dressing between periods of suction.

Looking next at FIGS. 42A-42D, there is shown another mechanical vacuum dressing 300A formed in accordance with the present invention. Mechanical vacuum dressing 300A is generally similar to the aforementioned mechanical vacuum dressing 300, except that arcuate support member 350A may be depressed by a finger of medical personnel and the finger moved from left-to-right while maintaining downward pressure, causing air to be drawn from opening 315A and absorptive material layer 330A, along first passageway 335A and out second passageways 345A. When pressure on first passageway 335A is relaxed, second passageways 345A close so as to maintain suction on the wound, i.e., mimicking the positive displacement feature of a peristaltic pump mechanism.

In this form of the invention, chamber 340A may have a low profile (i.e., its dome may be omitted), since negative pressure is established in opening 315A by the depression of arcuate support member 350A rather than the depression of the dome of chamber 340A.

Additional Comments

Thus it will be seen that, with the present invention, to dress a closed surgical wound, the mechanical vacuum dressing is first placed over the wound and adhered to the skin of a patient. Then medical personnel may activate negative pressure for the mechanical vacuum dressing by activating an associated mechanical pump. Depending on the pump configuration, the pump may be activated by (i) several pull and release motions on the mechanical vacuum dressing (e.g., for the aforementioned mechanical vacuum dressings 5, 5A, 5B, 5C, 5D, 5E and 5F), or (ii) by twisting a handle on a peristaltic pump mechanism (e.g., for the aforementioned mechanical vacuum dressing 5G), or (iii) by manually squeezing out air (e.g., for the aforementioned mechanical vacuum dressings 300 and 300A). Where a pressure gauge is provided, once sufficient negative pressure is achieved, the pressure gauge will create a visual change (e.g., bubble indicator, color change indicator, or other indication) to indicate sufficient negative pressure has been established within the mechanical vacuum dressing. The mechanical vacuum dressing is intended to maintain negative pressure for 1-2 days, during which time the pump associated with the mechanical vacuum dressing may be re-activated if, and when, needed. After 1-2 days, medical personnel may remove the mechanical vacuum dressing and, upon discharge of the patient, recommend that the patient follow standards of home wound care.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A mechanical vacuum dressing comprising:
  a first valve layer for disposition over a wound, the first valve layer comprising a first one-way valve;
  a second valve layer comprising a second one-way valve;
  the second valve layer being disposed over the first valve layer and joined to the first valve layer so as to define a chamber therebetween;
  the first one-way valve being configured to admit fluid into the chamber through the first one-way valve but prevent fluid from exiting the chamber through the first one-way valve;
  the second one-way valve being configured to exhaust fluid from the chamber through the second one-way valve but prevent fluid from entering the chamber through the second one-way valve; and
  the second valve layer comprising an elastomeric material such that (i) when the second valve layer is moved away from the first valve layer, the volume of the chamber is increased, and (ii) when the second valve layer is thereafter released, the second valve layer moves back towards the first valve layer and the volume of the chamber is decreased.

2. The mechanical vacuum dressing according to claim 1 further comprising an adhesive carried by the first valve layer.

3. The mechanical vacuum dressing according to claim 2 wherein the adhesive comprises a flexible material having an opening, and further wherein the first one-way valve opens on the opening.

4. The mechanical vacuum dressing according to 2 wherein the adhesive comprises an adhesive layer defining an opening, and further wherein the adhesive layer is mounted to the first valve layer.

5. The mechanical vacuum dressing according to claim 2 further comprising a peel-away liner removably disposed on the adhesive.

6. The mechanical vacuum dressing according to claim 3 further comprising an absorbent dressing disposed in the opening.

7. The mechanical vacuum dressing according to claim 6 wherein the absorbent dressing comprises at least one from the group consisting of a woven dressing, a non-woven dressing, and a foam dressing.

8. The mechanical vacuum dressing according to claim 6 wherein the absorbent dressing comprises at least one from the group consisting of antimicrobials, growth factors and other healing agents.

9. The mechanical vacuum dressing according to claim 1 further comprising an element mounted to the second valve layer, wherein the element is configured to be grasped by a user in order to pull the second valve layer away from the first valve layer.

10. The mechanical vacuum dressing according to claim 9 wherein the element and the second one-way valve are part of a single structure.

11. The mechanical vacuum dressing according to claim 9 wherein the element is selectively detachable from the second valve layer.

12. The mechanical vacuum dressing according to claim 1 wherein the first valve layer comprises an outer sublayer comprising at least one slit, and an inner sublayer comprising at least one flap, wherein the at least one flap is configured to selectively cover the at least one slit so as to form the first one-way valve.

13. The mechanical vacuum dressing according to claim 1 wherein the first valve layer comprises an outer sublayer comprising at least one slit, and an inner sublayer comprising at least one slit, wherein the inner sublayer and the outer sublayer are configured to selectively move relative to one another so as to form the first one-way valve.

14. A mechanical vacuum dressing comprising:
a first valve layer comprising a flat planar sheet and a first one-way valve;
a second valve layer comprising a flat planar sheet and a second one-way valve;
the first valve layer being joined to the second valve layer so as to define a chamber therebetween;
the first one-way valve being configured to admit fluid into the chamber through the first one-way valve but prevent fluid from exiting the chamber through the first one-way valve;
the second one-way valve being configured to exhaust fluid from the chamber through the second one-way valve but prevent fluid from entering the chamber through the second one-way valve; and
the second valve layer comprising an elastomeric material such that (i) when the second valve layer is moved away from the first valve layer, the volume of the chamber is increased, and (ii) when the second valve layer is thereafter released, the second valve layer moves back towards the first valve layer and the volume of the chamber is decreased.

15. The mechanical vacuum dressing according to claim 14 further comprising an adhesive carried by the first valve layer.

16. The mechanical vacuum dressing according to claim 15 wherein the adhesive comprises a flexible material having an opening, and further wherein the first one-way valve opens on the opening.

17. The mechanical vacuum dressing according to claim 15 wherein the adhesive comprises an adhesive layer defining an opening, and further wherein the adhesive layer is mounted to the first valve layer.

18. The mechanical vacuum dressing according to claim 15 further comprising a peel-away liner removably disposed on the adhesive.

19. The mechanical vacuum dressing according to claim 16 further comprising an absorbent dressing disposed in the opening.

20. The mechanical vacuum dressing according to claim 19 wherein the absorbent dressing comprises at least one from the group consisting of a woven dressing, a non-woven dressing, and a foam dressing.

21. The mechanical vacuum dressing according to claim 19 wherein the absorbent dressing comprises at least one from the group consisting of antimicrobials, growth factors and other healing agents.

22. The mechanical vacuum dressing according to claim 14 further comprising an element mounted to the second valve layer, wherein the element is configured to be grasped by a user in order to pull the second valve layer away from the first valve layer.

23. The mechanical vacuum dressing according to claim 22 wherein the element and the second one-way valve are part of a single structure.

24. The mechanical vacuum dressing according to claim 22 wherein the element is selectively detachable from the second valve layer.

25. The mechanical vacuum dressing according to claim 14 wherein the first valve layer comprises an outer sublayer comprising at least one slit, and an inner sublayer comprising at least one flap, wherein the at least one flap is configured to selectively cover the at least one slit so as to form the first one-way valve.

26. The mechanical vacuum dressing according to claim 14 wherein the first valve layer comprises an outer sublayer comprising at least one slit, and an inner sublayer comprising at least one slit, wherein the inner sublayer and the outer sublayer are configured to selectively move relative to one another so as to form the first one-way valve.

27. The mechanical vacuum dressing according to claim 14 wherein the first valve layer and the second valve layer are substantially parallel to one another before the second valve layer is moved away from the first valve layer.

* * * * *